US012797439B2

(12) United States Patent
Wimley et al.

(10) Patent No.: US 12,797,439 B2
(45) **Date of Patent: *Nov. 17, 2026**

(54) PEPTIDE COMPOSITIONS AND METHODS OF USE THEREOF

(71) Applicant: The Administrators of the Tulane Educational Fund, New Orleans, LA (US)

(72) Inventors: William Charles Wimley, New Orleans, LA (US); Charles Gannon Starr, New Orleans, LA (US); Shantanu Guha, New Orleans, LA (US); Jenisha Ghimire, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 923 days.

This patent is subject to a terminal disclaimer.

(21) Appl. No.: 17/796,950

(22) PCT Filed: Feb. 12, 2021

(86) PCT No.: PCT/US2021/018031

§ 371 (c)(1),
(2) Date: Aug. 2, 2022

(87) PCT Pub. No.: WO2021/163620

PCT Pub. Date: Aug. 19, 2021

(65) Prior Publication Data

US 2023/0310540 A1 Oct. 5, 2023

Related U.S. Application Data

(60) Provisional application No. 62/976,694, filed on Feb. 14, 2020.

(51) Int. Cl.

| | |
|---|---|
| ***A61K 38/00*** | (2006.01) |
| ***A01N 63/50*** | (2020.01) |
| ***A01P 1/00*** | (2006.01) |
| ***A61K 9/00*** | (2006.01) |
| ***A61K 38/12*** | (2006.01) |
| ***A61K 45/06*** | (2006.01) |
| ***A61P 17/02*** | (2006.01) |
| ***A61P 31/04*** | (2006.01) |
| ***C07K 7/64*** | (2006.01) |

(52) U.S. Cl.

CPC .............. *A61K 38/12* (2013.01); *A01N 63/50* (2020.01); *A01P 1/00* (2021.08); *A61K 9/0014* (2013.01); *A61K 45/06* (2013.01); *A61P 17/02* (2018.01); *A61P 31/04* (2018.01); *C07K 7/64* (2013.01)

(58) Field of Classification Search

CPC ...... A01N 63/50; A61K 9/0014; A61K 45/06; A61K 38/12; A61P 17/02; A61P 31/04; C07K 7/64; A01P 1/00

See application file for complete search history.

(56) References Cited

U.S. PATENT DOCUMENTS

| | | | |
|---|---|---|---|
| 6,620,923 B1 | 9/2003 | Specht et al. | |
| 7,745,391 B2 | 6/2010 | Mintz et al. | |
| 11,149,068 B2 | 10/2021 | Wimley et al. | |
| 11,266,743 B2 | 3/2022 | Wimley et al. | |
| 2004/0123343 A1 | 6/2004 | La Rosa et al. | |
| 2004/0147027 A1 | 7/2004 | Troy et al. | |
| 2009/0099533 A1 | 4/2009 | Montelaro et al. | |
| 2009/0203611 A1 | 8/2009 | Zhang et al. | |
| 2009/0317395 A1 | 12/2009 | Kofler et al. | |
| 2011/0110937 A1 | 5/2011 | Simon | |
| 2011/0150917 A1 | 6/2011 | Hancock et al. | |
| 2011/0265221 A1* | 10/2011 | Abad ................ | C12N 15/8273 435/317.1 |
| 2012/0017292 A1 | 1/2012 | Kovalic et al. | |
| 2012/0178649 A1 | 7/2012 | Watt et al. | |
| 2014/0024597 A1 | 1/2014 | Troy et al. | |
| 2019/0192691 A1 | 6/2019 | Barrett et al. | |
| 2019/0211063 A1 | 7/2019 | Wimley et al. | |
| 2019/0292234 A1 | 9/2019 | Bachnoff et al. | |
| 2020/0276322 A1 | 9/2020 | Wimley et al. | |

FOREIGN PATENT DOCUMENTS

| | | |
|---|---|---|
| CA | 2991223 A1 | 7/2019 |
| EP | 1724280 A1 | 11/2006 |
| EP | 2394665 A1 | 12/2011 |
| WO | WO-2011/056212 A1 | 5/2011 |
| WO | WO-2016/142445 A2 | 9/2016 |

(Continued)

OTHER PUBLICATIONS

Akinc et al., "Exploring polyethylenimine-mediated DNA transfection and the proton sponge hypothesis," J Gene Med. 7(5):657-663 (2005).
An et al., "pH-(low)-insertion-peptide (pHLIP) translocation of membrane impermeable phalloidin toxin inhibits cancer cell proliferation," Proc Natl Acad Sci U S A. 107(47):20246-20250 (2010).
Andreev et al., "pH-sensitive membrane peptides (pHLIPs) as a novel class of delivery agents," available in PMC Dec. 25, 2015, published in final edited form as: Mol Membr Biol. 27(7):341-352 (2010) (21 pages).
Anonymous, "UPI0007A1D356," UniParc, UniProt. Accessed Dec. 2, 2024, (Apr. 2016) (4 pages).
Atherton et al., "Solid-Phase Peptide Synthesis: A Practical Approach," Febs Letters. 265(1,2):152 (1990) (1 page).
Badani et al., "Peptide entry inhibitors of enveloped viruses: the importance of interfacial hydrophobicity," Biochim Biophys Acta. 1838(9):2180-97 (Sep. 2014).
Bechinger, "Peptide-nucleic acid nanostructures for transfection," Biomol Concepts. 3(3):283-293 (2012).

(Continued)

*Primary Examiner* — Melissa L Fisher
*Assistant Examiner* — Sara E Konopelski Snavely
(74) *Attorney, Agent, or Firm* — Womble Bond Dickinson (US) LLP

(57) ABSTRACT

Described herein are antimicrobial peptides, polynucleotides encoding the peptides, and compositions containing the peptides. Furthermore, described herein are methods for using the peptides, polynucleotides, and compositions for research and therapy.

19 Claims, 5 Drawing Sheets
(1 of 5 Drawing Sheet(s) Filed in Color)

Specification includes a Sequence Listing.

(56) References Cited

FOREIGN PATENT DOCUMENTS

WO WO-2018/091523 A1 5/2018
WO WO-2019084343 A1 * 5/2019 .............. A61P 31/04

OTHER PUBLICATIONS

Bechinger, "Structure and function of membrane-lytic peptides," Critical Reviews in Plant Sciences. 23(3):1-22 (2004) (23 pages).
Brown et al., "Cationic host defense (antimicrobial) peptides," Curr Opin Immunol. 18(1): 24-30 (2006).
Chang et al., "Characterization of antimicrobial peptide activity by electrochemical impedance spectroscopy," available in PMC Oct. 1, 2009, published in final edited form as: Biochim Biophys Acta. 1778(10):2430-36 (2008) (16 pages).
Chen et al., "Simulation-Guided Rational de Novo Design of a Small Pore-Forming Antimicrobial Peptide," J Am Chem Soc. 141(12):4839-48 (2019) (1 page) (Abstract only).
Dempsey, "The action of melittin on membranes," Biochim Biophys Acta. 1031(2):143-161 (1990).
Duncan, "The dawning era of polymer therapeutics," Nat Rev Drug Discov. 2(5):347-360 (2003).
Endoh et al., "Cellular siRNA delivery using cell-penetrating peptides modified for endosomal escape," Adv Drug Deliv Rev. 61(9):704-709 (2009).
Erazo-Oliveras et al., "Improving the endosomal escape of cell-penetrating peptides and their cargos: strategies and challenges," Pharmaceuticals (Basel). 5(11):1177-1209 (2012).
Extended European Search Report for European Patent Application No. 18871046.1 dated Oct. 22, 2021 (13 pages).
Extended European Search Report for European Patent Application No. 21754083.0 dated Jan. 29, 2024 (8 pages).
Extended European Search Report for European Patent Application No. 21780752.8, dated Feb. 23, 2024 (22 pages).
Farrand et al., "The Cholesterol-dependent Cytolysin Membrane-binding Interface Discriminates Lipid Environments of Cholesterol to Support beta-Barrel Pore Insertion," J Biol Chem. 290(29): 17733-44 (2015).
Fendos et al., "Aspartate Embedding Depth Affects pHLIP's Insertion pKa," available in PMC Jul. 9, 2014, published in final edited form as: Biochemistry. 52(27):4595-4604 (2013).
Ganz et al., "Defensins," Eur J Haematol. 44(1):1-8 (1990).
Gerlach et al., "Anticancer and chemosensitizing abilities of cycloviolacin 02 from Viola odorata and psyle cyclotides from Psychotria leptothyrsa," Biopolymers. 94(5):617-25 (2010).
Gillies et al., "Causes and consequences of increased glucose metabolism of cancers," J Nucl Med. 49(Suppl 2):24S-42S (2008) (20 pages).
He et al., "A Lack of Synergy Between Membrane-permeabilizing Cationic Antimicrobial Peptides and Conventional Antibiotics," available in PMC Jan. 1, 2016, published in final edited form as: Biochim Biophys Acta. 1848(100):8-15 (2015) (21 pages).
He et al., "Novel Antiviral Agents: Design, Identification and Characterization of Interfacially Active Peptide Entry inhibitors," FASEB J. 29(S1):886.20 (Apr. 2015) (2 pages).
He et al., "Toward the de novo design of antimicrobial peptides: Lack of correlation between peptide permeabilization of lipid vesicles and antimicrobial, cytolytic, or cytotoxic activity in living cells," available in PMC Jan. 1, 2015, published in final edited form as: Biopolymers. 102(1):1-6 (2014) (10 pages).
Heitz et al., "Twenty years of cell-penetrating peptides: from molecular mechanisms to therapeutics," Br J Pharmacol. 157(2):195-206 (2009).
Hoffmann et al., "Broad-Spectrum Antiviral Entry Inhibition by Interfacially Active Peptides," J Virol. 94(23):e01682-20 (Nov. 2020) (20 pages).
Hoffmann, "Randomly Selected Hydrophobic Peptide Inhibit Lassa Pseudovirus," Biophys J. 108(2):83a (Feb. 2015) (1 page).
Hoffmann, Andrew Robert, Dissertation: "Discovery and Design of Broad-Spectrum Antiviral Peptides," Ph.D., Tulane University, Mar. 2020 (194 pages).
Hristova et al., "A look at arginine in membranes," available in PMC Jan. 1, 2012, published in final edited form as: J Membr Biol. 239(1-2):49-56 (2011) (13 pages).
Hällbrink et al., "Cargo delivery kinetics of cell-penetrating peptides," Biochim Biophys Acta. 1515(2):101-109 (2001).
International Preliminary Report on Patentability for International Application No. PCT/US18/57614, mailed Feb. 25, 2019 (7 pages).
International Search Report and Written Opinion for International Application No. PCT/US18/57614, mailed Feb. 25, 2019 (17 pages).
Kakudo et al., "Transferrin-Modified Liposomes Equipped with a pH-Sensitive Fusogenic Peptide: An Artificial Viral-like Delivery System," Biochemistry. 43(19):5618-5628 (2004) (11 pages).
Kauffman et al., "Mechanism Matters: A Taxonomy of Cell Penetrating Peptides," available in PMC Dec 1, 2016, published in final edited form as: Trends Biochem Sci. 40(12):749-764 (2015) (28 pages).
Komin et al., "Peptide-based strategies for enhanced cell uptake, transcellular transport, and circulation: Mechanisms and challenges," Adv Drug Deliv Rev. 110-111:52-64 (2017).
Krauson et al., "Conformational Fine-Tuning of Pore-Forming Peptide Potency and Selectivity," J Am Chem Soc 137(51): 16144-52 (2015).
Krauson et al., "Determining the mechanism of membrane permeabilizing peptides: Identification of potent, equilibrium pore-formers," available in PMC Jul. 1, 2013, published in final edited form as: Biochim Biophys Acta. 1818(7):1625-32 (2012) (20 pages).
Krauson et al., "Gain-of-Function Analogues of the Pore-Forming Peptide Melittin Selected by Orthogonal High-Throughput Screening," available in PMC Aug. 1, 2013, published in final edited form as: J Am Chem Soc 134(30):12732-12741 (2012) (20 pages).
Krauson et al., "Synthetic molecular evolution of pore-forming peptides by Iterative combinatorial library screening," available in PMC Apr. 19, 2014, published in final edited form as: ACS Chem Biol. 8(4):823-31 (2013) (18 pages).
Kullberg et al., "Listeriolysin O enhances cytoplasmic delivery by Her-2 targeting liposomes," J Drug Target. 18(4):313-320 (2010) (9 pages).
Ladokhin et al., "Leakage of Membrane Vesicle Contents: Determination of Mechanism Using Fluorescence Requenching," Biophys J. 69(5):1964-71 (1995).
Lam et al., "Effective endogenous gene silencing mediated by pH responsive peptides proceeds via multiple pathways," available in PMC Mar. 21, 2012, published in final edited form as: J Control Release. 158(2):293-303 (2012) (23 pages).
Lehrer et al., "Defensins: Endogenous Antibiotic Peptides of Animal Cells," Cell. 64(2):229-230 (1991) (2 pages).
LifeTein, "The Cationic Host Defense Peptides Could Be Used to Kill Enveloped Novel Coronavirus SARS-CoV-2", <URL:https://www.lifetein.com/blog/the-cationic-host-defense-peptides-could-be-used-to-kill-enveloped-novel-coronavirus-sars-cov-2/>, dated Feb. 28, 2020, retrieved Jul. 1, 2021 (5 pages).
Lin et al., "Interactions of membrane active peptides with planar supported bilayers: an impedance spectroscopy study," Langmuir. 28(14):6088-96 (2012) (1 page) (Abstract only).
Maiolo et al., "Specific Redistribution of Cell-Penetrating Peptides from Endosomes to the Cytoplasm and Nucleus upon Laser Illumination," J Am Chem Soc 126(47):15376-15377 (2004) (2 pages).
Mayer et al., "Vesicles of variable sizes produced by a rapid extrusion procedure," Biochim Biophys Acta. 858(1):161-168 (1986).
Muro, "Challenges in design and characterization of ligand-targeted drug delivery systems," available in PMC Dec. 10, 2013, available in final edited form as: J Control Release. 164(2):125-137 (2012) (33 pages).
Nishimura et al., "A display of pH-sensitive fusogenic GALA peptide facilitates endosomal escape from a Bio-nanocapsule via an endocytic uptake pathway," J Nanobiotechnology. 12:11 (2014) (6 pages).
Office Action for Canadian Patent Application No. 3,167,422, dated Jan. 24, 2024 (5 pages).

(56) References Cited

OTHER PUBLICATIONS

Oliveira et al., "Fusogenic peptides enhance endosomal escape improving siRNA-induced silencing of oncogenes," Int J Pharm. 331(2):211-214 (2007).
Pantaleo et al., "Molecular imaging and targeted therapies in oncology: New concepts in treatment response assessment. A collection of cases," Int J Oncol. 33(3):443-452 (2008).
Parente et al., "Mechanism of Leakage of Phospholipid Vesicle Contents Induced by the Peptide GALA," Biochemistry. 29(37): 8720-8728 (1990) (9 pages).
Parente et al., "Association of a pH-Sensitive Peptide with Membrane Vesicles: Role of Amino Acid Sequence," Biochemistry. 29(37): 8713-8719 (1990) (7 pages).
Rathinakumar et al., "Biomolecular engineering by combinatorial design and high-throughput screening: small, soluble peptides that permeabilize membranes," available in PMC Nov. 13, 2008, published in final edited form as: J Am Chem Soc. 130(30):9849-9858 (2008) (26 pages).
Rathinakumar et al., "Broad-spectrum Antimicrobial Peptides by Rational Combinatorial Design and High-throughput Screening: The Importance of Interfacial Activity," available in PMC Sep. 8, 2010, published in final edited form as: J Am Chem Soc. 131(22):7609-17 (2009) (23 pages).
Rathinakumar et al., "High-throughput discovery of broad-spectrum peptide antibiotics," FASEB J. 24(9):3232-38 (2010) (11 pages).
Rausch et al., "A high-throughput screen for identifying transmembrane pore-forming peptides," Anal Biochem. 293(2):258-63 (2001).
Rausch et al., "Beta-Sheet Pore-Forming Peptides Selected from a Rational Combinatorial Library: Mechanism of Pore Formation in Lipid Vesicles and Activity in Biological Membranes," available in PMC Nov. 14, 2008, published in final edited form as: Biochemistry. 46(43):12124-39 (2007) (37 pages).
Rausch et al., "Rational combinatorial design of pore-forming beta-sheet peptides," Proc Natl Acad Sci U S A. 102(30):10511-10515 (2005).
Räägel et al., "Peptide-mediated protein delivery—Which pathways are penetrable?" Biochim Biophys Acta. 1798(12):2240-2248 (2010).
Shai et al., "From 'carpet' mechanism to de-novo designed diastereomeric cell-selective antimicrobial peptides," Peptides. 22(10):1629-1641 (2001).
Snider et al., "MPEx: A tool for exploring membrane proteins," Protein Sci. 18(12):2624-2628 (2009).
Soman et al., "Molecularly targeted nanocarriers deliver the cytolytic peptide melittin specifically to tumor cells in mice, reducing tumor growth," J Clin Invest. 119(9):2830-2842 (2009).
Starr et al., "Antimicrobial peptides are degraded by the cytosolic proteases of human erythrocytes," available in PMC Dec 1, 2018, published in final edited form as: Biochim Biophys Acta. 1859(12):2319-26 (2017) (20 pages).
Starr et al., "Host Cell Interactions are a Significant Barrier to the Clinical Utility of Peptide Antibiotics," available in PMC Jul. 21, 2017, published in final edited form as: ACS Chem Biol. 11(12):3391-99 (2016) (18 pages).
Starr et al., "Pituitary adenylate cyclase-activating polypeptide is a potent broad-spectrum antimicrobial peptide: Structure-activity relationships," available in PMC Jun. 1, 2019, published in final edited form as: Peptides. 104:35-40 (2018) (19 pages).
Subbarao et al., "pH-Dependent Bilayer Destabilization by an Amphipathic Peptide," Biochemistry. 26(11):2964-2972 (1987) (9 pages).
Supplementary Partial European Search Report for European Patent Application No. 18871046.1, dated Jul. 22, 2021 (15 pages).
Van Dyke, "Acidification of Lysosomes and Endosomes," Subcell Biochem. 27:331-360 (1996) (30 pages).
Varkouhi et al., "Endosomal escape pathways for delivery of biologicals," J Control Release. 151(3):220-228 (2011).
Walkenhorst et al., "pH Dependence of Microbe Sterilization by Cationic Antimicrobial Peptides," Antimicrob Agents Chemother. 57(7) 2013:3312-20 (2013).
Wang et al., "Burkholderia thailandensis outer membrane vesicles exert antimicrobial activity against drug-resistant and competitor microbial species," J Microbiol. 58(7):550-62 (Jul. 2020) (1 page) (Abstract only).
White et al., "Protein folding in membranes: Determining the energetics of peptide-bilayer interactions," Methods Enzymol. 295:62-87 (1998).
White et al., "Structure, function, and membrane integration of defensins," Curr Opin Struct Biol. 5(4):521-7 (1995) (1 page) (Abstract only).
Wiedman et al., "Highly Efficient Macromolecule-Sized Poration of Lipid Bilayers by a Synthetically Evolved Peptide," J Am Chem Soc. 136(12): 4724-31 (2014).
Wiedman et al., "PH-Triggered, Macromolecule-Sized Poration of Lipid Bilayers by Synthetically Evolved Peptides," available in PMC Jul. 21, 2017, published in final edited form as: J Am Chem Soc 139(2):937-45 (2017) (22 pages).
Wiedman et al., "Testing the limits of rational design by engineering pH sensitivity into membrane active peptides," available in PMC Apr. 1, 2016, published in final edited form as: Biochim Biophys Acta. 1848(4):951-7 (2015) (15 pages).
Wiedman et al., "The electrical response of bilayers to the bee venom toxin melittin: Evidence for transient bilayer permeabilization," available in PMC May 14, 2014, published in final edited form as: Biochim Biophys Acta. 1828(5):1357-1364 (2013) (21 pages).
Wimley et al., "Antimicrobial Peptides: successes, challenges and unanswered questions," available in PMC Sep. 2, 2011, published in final edited form as: J Membr Biol. 239(1-2):27-34 (2011) (12 pages).
Wimley et al., "Determining the membrane topology of peptides by fluorescence quenching," Biochemistry. 39(1):161-70 (2000).
Wimley et al., "Folding of beta-sheet membrane proteins: a hydrophobic hexapeptide model," J Mol Biol. 277(5):1091-1110 (1998).
Wimley et al., "Interactions between human defensins and lipid bilayers: evidence for formation of multimeric pores," Protein Sci. 3(9):1362-73 (1994).
Wimley et al., "The Mechanism of Membrane Permeabilization by Peptides: Still an Enigma," available in PMC Apr. 27, 2020, published in final edited form as: Aust J Chem. 73(3):96-103 (2019) (16 pages).
Wimley, "Application of Synthetic Molecular Evolution to the Discovery of Antimicrobial Peptides," available in PMC Oct. 8, 2019, published in final edited form as: Adv Exp Med Biol. 1117: 241-255 (2019) (20 pages).
Wimley, "Describing the Mechanism of Antimicrobial Peptide Action with the Interfacial Activity Model," available in PMC Oct. 15, 2011, published in final edited form as: ACS Chem Biol. 15(10):905-17 (2010) (21 pages).
Wimley, "Energetics of peptide and Protein Binding to Lipid Membranes," Adv Exp Med Biol. 677:14-23 (2010) (10 pages).
Yao et al., "pHLIP®-mediated delivery of PEGylated liposomes to cancer cells," available in PMC May 10, 2014, published in final edited form as: J Control Release. 167(3):228-237 (2013) (24 pages).
Yu et al., "Overcoming Endosomal Barrier by Amphotericin B-Loaded Dual pH-Responsive PDMA-b-PDPA Micelleplexes for siRNA Delivery," available in PMC Mar. 18, 2016, published in final edited form as: ACS Nano. 5(11):9246-9255 (2011) (21 pages).
International Preliminary Report on Patentability for International Patent Application No. PCT/US2021/018031, issued Aug. 11, 2022 (11 pages).
International Search Report and Written Opinion for International Patent Application No. PCT/US2021/018031, mailed May 13, 2021 (14 pages).
Starr et al., "Synthetic molecular evolution of host cell-compatible, antimicrobial peptides effective against drug-resistant, biofilm-forming bacteria," Proc Natl Acad Sci USA. 117(15):8437-8448. (Apr. 2020).

* cited by examiner

Vehicle Treated

D-CONGA-Q7 Treated

SEQUENCE LISTING

```
<160> NUMBER OF SEQ ID NOS: 29

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg
```

<400> SEQUENCE: 1

Xaa Xaa Xaa Xaa Xaa Xaa Xaa Xaa Xaa Xaa Xaa Xaa Xaa
1 5 10

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Arg Arg Trp Ala Arg Arg Leu Ala Phe Ala Phe Arg Arg
1 5 10

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Gly
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Phe
<220> FEATURE:
<221> NAME/KEY: MISC_FEATURE
<222> LOCATION: (13)..(14)
<223> OTHER INFORMATION: Xaa is D-Arg

<400> SEQUENCE: 3

Xaa Xaa Xaa Xaa Xaa Xaa Xaa Xaa Xaa Xaa Xaa Xaa Xaa Xaa
1 5 10

<210> SEQ ID NO 4
<211> LENGTH: 14

<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-beta-alanine
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Phe
<220> FEATURE:
<221> NAME/KEY: MISC_FEATURE
<222> LOCATION: (13)..(14)
<223> OTHER INFORMATION: Xaa is D-Arg

<400> SEQUENCE: 4

```
Xaa Xaa Xaa Xaa Xaa Xaa Xaa Xaa Xaa Xaa Xaa Xaa Xaa Xaa
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Gln
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Phe
<220> FEATURE:
<221> NAME/KEY: MISC_FEATURE
<222> LOCATION: (13)..(14)
<223> OTHER INFORMATION: Xaa is D-Arg

<400> SEQUENCE: 5

Xaa Xaa Xaa Xaa Xaa Xaa Xaa Xaa Xaa Xaa Xaa Xaa Xaa Xaa
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(5)
<223> OTHER INFORMATION: Xaa is D-Arg
<220> FEATURE:
<221> NAME/KEY: MISC_FEATURE
<222> LOCATION: (6)..(6)
<223> OTHER INFORMATION: Xaa is D-Leu
<220> FEATURE:
<221> NAME/KEY: MISC_FEATURE
<222> LOCATION: (7)..(7)
<223> OTHER INFORMATION: Xaa is D-Ala
<220> FEATURE:
<221> NAME/KEY: MISC_FEATURE
<222> LOCATION: (8)..(8)
<223> OTHER INFORMATION: Xaa is D-Phe
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Phe
<220> FEATURE:
<221> NAME/KEY: MISC_FEATURE
<222> LOCATION: (11)..(12)
<223> OTHER INFORMATION: Xaa is D-Arg

<400> SEQUENCE: 6

Xaa Xaa Xaa Xaa Xaa Xaa Xaa Xaa Xaa Xaa Xaa Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(10)
<223> OTHER INFORMATION: Xaa is D-Phe
<220> FEATURE:
<221> NAME/KEY: MISC_FEATURE
<222> LOCATION: (11)..(12)
<223> OTHER INFORMATION: Xaa is D-Arg

<400> SEQUENCE: 7

Xaa Xaa Xaa Xaa Xaa Xaa Xaa Xaa Xaa Xaa Xaa Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Leu
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(5)
<223> OTHER INFORMATION: Xaa is D-Phe
<220> FEATURE:
<221> NAME/KEY: MISC_FEATURE
<222> LOCATION: (6)..(6)
<223> OTHER INFORMATION: Xaa is D-Ala
<220> FEATURE:

```
<221> NAME/KEY: MISC_FEATURE
<222> LOCATION: (7)..(7)
<223> OTHER INFORMATION: Xaa is D-Phe
<220> FEATURE:
<221> NAME/KEY: MISC_FEATURE
<222> LOCATION: (8)..(8)
<223> OTHER INFORMATION: Xaa is D-Trp
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(13)
<223> OTHER INFORMATION: Xaa is D-Arg

<400> SEQUENCE: 8

Xaa Xaa Xaa Xaa Xaa Xaa Xaa Xaa Xaa Xaa Xaa Xaa Xaa
1               5                   10


<210> SEQ ID NO 9
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(12)
<223> OTHER INFORMATION: Xaa is D-Arg

<400> SEQUENCE: 9

Xaa Xaa Xaa Xaa Xaa Xaa Xaa Xaa Xaa Xaa Xaa Xaa
1               5                   10


<210> SEQ ID NO 10
<211> LENGTH: 14
<212> TYPE: PRT
<213> ORGANISM: Artificial Sequence
```

<220> FEATURE:
<223> OTHER INFORMATION: Synthetic Construct

<400> SEQUENCE: 10

Arg Arg Trp Ala Arg Arg Leu Ala Phe Ala Phe Arg Arg Glu
1 5 10

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Arg Arg Trp Ala Arg Arg Leu Ala Phe Ala Phe Arg Arg
1 5 10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-homoarginine
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg

<400> SEQUENCE: 12

Xaa Xaa Xaa Xaa Xaa Xaa Xaa Xaa Xaa Xaa Xaa Xaa Xaa
1 5 10

<210> SEQ ID NO 13
<211> LENGTH: 13
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-norarginine
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg

<400> SEQUENCE: 13

Xaa Xaa Xaa Xaa Xaa Xaa Xaa Xaa Xaa Xaa Xaa Xaa Xaa
1               5                   10


<210> SEQ ID NO 14
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ala or absent
<220> FEATURE:
<221> NAME/KEY: MISC_FEATURE
<222> LOCATION: (5)..(5)
<223> OTHER INFORMATION: Xaa is Lys, Arg, or a derivative thereof
<220> FEATURE:
<221> NAME/KEY: MISC_FEATURE
<222> LOCATION: (6)..(6)
<223> OTHER INFORMATION: Xaa is Lys, Arg, or a derivative thereof
<220> FEATURE:
<221> NAME/KEY: MISC_FEATURE
<222> LOCATION: (7)..(7)
<223> OTHER INFORMATION: Xaa is Gly, Gln, beta-alanine, or absent
<220> FEATURE:
<221> NAME/KEY: MISC_FEATURE
<222> LOCATION: (11)..(11)
<223> OTHER INFORMATION: Xaa is Ala or absent
<220> FEATURE:
<221> NAME/KEY: MISC_FEATURE
<222> LOCATION: (14)..(14)
<223> OTHER INFORMATION: Xaa is Lys, Arg, or absent
```

<220> FEATURE:
<221> NAME/KEY: MISC_FEATURE
<222> LOCATION: (15)..(15)
<223> OTHER INFORMATION: Xaa is Asp, Glu, or absent

<400> SEQUENCE: 14

Arg Arg Trp Xaa Xaa Xaa Xaa Leu Ala Phe Xaa Phe Arg Xaa Xaa
1 5 10 15

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (6)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg

<400> SEQUENCE: 15

Xaa Xaa Xaa Xaa Arg Xaa Xaa Xaa Xaa Ala Xaa Xaa Xaa
1 5 10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is D-Arg
<220> FEATURE:
<221> NAME/KEY: MISC_FEATURE
<222> LOCATION: (13)..(13)
<223> OTHER INFORMATION: Xaa is D-Arg

<400> SEQUENCE: 16

Xaa Arg Trp Ala Arg Arg Leu Ala Phe Ala Phe Arg Xaa
1 5 10

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Arg Arg Trp Ala Arg Arg Gly Leu Ala Phe Ala Phe Arg Arg
1 5 10

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is beta-alanine

<400> SEQUENCE: 18

Arg Arg Trp Ala Arg Arg Xaa Leu Ala Phe Ala Phe Arg Arg
1 5 10

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Arg Arg Trp Ala Arg Arg Gln Leu Ala Phe Ala Phe Arg Arg
1 5 10

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Arg Arg Trp Arg Arg Leu Ala Phe Ala Phe Arg Arg
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Arg Arg Trp Ala Arg Arg Leu Ala Phe Phe Arg Arg
1 5 10

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Arg Arg Leu Ala Phe Ala Phe Trp Ala Arg Arg Arg Arg
1 5 10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Arg Arg Trp Ala Arg Arg Leu Ala Phe Ala Phe Arg
1 5 10

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg
<220> FEATURE:
<221> NAME/KEY: MISC_FEATURE
<222> LOCATION: (14)..(14)
<223> OTHER INFORMATION: Xaa is D-Glu

<400> SEQUENCE: 24

Xaa Xaa Xaa Xaa Xaa Xaa Xaa Xaa Xaa Xaa Xaa Xaa Xaa Xaa
1 5 10

<210> SEQ ID NO 25
<211> LENGTH: 13

<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(13)
<223> OTHER INFORMATION: Xaa is D-Arg

<400> SEQUENCE: 25

```
Xaa Xaa Xaa Xaa Xaa Xaa Xaa Xaa Xaa Xaa Xaa Xaa Xaa
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(6)
<223> OTHER INFORMATION: Xaa is homoarginine

<400> SEQUENCE: 26

```
Arg Arg Trp Ala Xaa Xaa Leu Ala Phe Ala Phe Arg Arg
1               5                   10
```

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(6)
<223> OTHER INFORMATION: Xaa is norarginine

<400> SEQUENCE: 27

Arg Arg Trp Ala Xaa Xaa Leu Ala Phe Ala Phe Arg Arg
1 5 10

<210> SEQ ID NO 28
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is D-Arg
<220> FEATURE:
<221> NAME/KEY: MISC_FEATURE
<222> LOCATION: (10)..(10)
<223> OTHER INFORMATION: Xaa is D-Ala

<400> SEQUENCE: 28

Arg Arg Trp Ala Xaa Arg Leu Ala Phe Xaa Phe Arg Arg
1 5 10

<210> SEQ ID NO 29
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (5)..(6)
<223> OTHER INFORMATION: Xaa is D-Arg
<220> FEATURE:
<221> NAME/KEY: MISC_FEATURE
<222> LOCATION: (7)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (9)..(9)
<223> OTHER INFORMATION: Xaa is D-Phe
<220> FEATURE:
<221> NAME/KEY: MISC_FEATURE
<222> LOCATION: (10)..(10)
<223> OTHER INFORMATION: Xaa is D-Ala
<220> FEATURE:
<221> NAME/KEY: MISC_FEATURE
<222> LOCATION: (11)..(11)
<223> OTHER INFORMATION: Xaa is D-Phe
<220> FEATURE:
<221> NAME/KEY: MISC_FEATURE
<222> LOCATION: (12)..(12)
<223> OTHER INFORMATION: Xaa is D-Arg

<400> SEQUENCE: 29

Arg Xaa Xaa Xaa Xaa Xaa Xaa Xaa Xaa Xaa Xaa Xaa Arg
1 5 10

PEPTIDE COMPOSITIONS AND METHODS OF USE THEREOF

STATEMENT REGARDING FEDERALLY SPONSORED RESEARCH

This invention was made with government support under Grant Nos. R01GM111824, R01GM60000, and R21AI119104, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Feb. 12, 2021, is named 07005-021WO2_Sequence_Listing_2_12_2021_ST25 and is 17,555 bytes in size.

BACKGROUND

With rapidly increasing emergence of antibiotic-resistant bacteria, the development of novel antibiotics is extremely important to the medical field. The mechanism of action of antimicrobial peptides (AMPS), plasma membrane destabilization, makes them less likely to elicit resistant phenotypes. Gram-negative bacteria are notoriously difficult to treat with traditional small molecule antibiotics. Thus, there exists a need to develop novel peptides that are effective against difficult to treat microbes, in particular, Gram-negative pathogens.

SUMMARY OF THE DISCLOSURE

A first aspect of the disclosure features polypeptides with at least 85% (e.g., at least 90%, 95%, 97%, or 100%) sequence identity to the sequence of any one of SEQ ID NOS: 3-29. In some embodiments, the polypeptides have at least 85% (e.g., at least 90%, 95%, 97%, or 100%) sequence identity to the sequence of any one of SEQ ID NOS: 3-14. In particular, the polypeptide has the sequence of SEQ ID NO: 5. The polypeptides are antimicrobial peptides, such as polypeptides exhibiting an ability to disrupt the cellular membrane of a microbial pathogen (e.g., *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium* lentum, *Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia,*

*Streptococcus agalactiae, Streptococcus constellatus, Streptococcus pneumoniae* (penicillin susceptible and resistant isolates), *Streptococcus pyogenes*, or *Streptococcus pyogenes*) and/or a fungal pathogen (e.g., from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp., *Pilaira* spp., *Rhizomucor* spp., *Rhizopus* spp., or *Zygomycetes* spp.), and phylum Oomycota in the Stramenopila kingdom).

The polypeptides may also have one or more D-amino acids (e.g., D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL), one or more L-amino acids, or a mixture of D- and L-amino acids. The polypeptides can also have one or more derivatized amino acids (e.g., N-imbenzylhistidine, 4-hydroxyproline, 5-hydroxylysine, 3-methylhistidine, homoserine, and ornithine). The polypeptides may also have a chemical moiety (e.g., amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl). The polypeptides may be 10-20 amino acids long (e.g., 10, 11, 12, 13, 14, 15, 16, 17, 18, 19, or 20 amino acids). The polypeptides may also be cyclized.

A second aspect of the disclosure features a polynucleotide encoding the polypeptide of the first aspect.

A third aspect of the disclosure features a vector containing the polynucleotide of the second aspect encoding the polypeptide of the first aspect.

A fourth aspect of the disclosure features a composition comprising the polypeptide of the first aspect, the polynucleotide of the second aspect, or the vector of the third aspect. The composition may also include a pharmaceutically acceptable carrier, excipient, or diluent. The composition may further include a therapeutic agent. In particular, the therapeutic agent can be an antimicrobial agent, such as an antifungal agent (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosin, griseofulvin, haloprogin, tolnaftate, aminocandin, chlordantoin, chlorphenesin, nifuroxime, undecylenic acid, and crystal violet, and pharmaceutically acceptable salts or esters thereof. In some embodiments the composition of the fourth aspect is a liquid or a solid. In certain embodiments, the polypeptide in the composition of the fourth aspect of the invention is incorporated in the composition or coated thereon. In some embodiments, the composition of the fourth aspect is incorporated into a medical device, a cuff, a dressing material, a mesh, a hernia patch, a wound dressing, a bandage, a syringe, gloves, or a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface.

A fifth aspect of the disclosure features a method of treating a microbial infection by administering the composition of the fourth aspect to a subject (e.g., a human or animal, e.g., a mammal, such as a bovine, equine, canine, ovine, and feline) with an infection. In particular, the microbial infection can be a fungal infection (e.g., *Fusarium oxysporum, Pneumocystis jirovecii, Aspergillus* spp., *Coccidioides immitis/posadasii, Candida* sp., *Filobasidiella neoformans, Trichosporon, Encephalitozoon cuniculi, Enterocytozoon bieneusi, Mucor circinelloides, Rhizopus oryzae*, and *Lichtheimia corymbifera*), or a bacterial infection (e.g., *Acinetobacter baumannii, Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus*, spp. *Escherichia coli, Eubacterium lentum, Fusobacterium* spp., *Haemophilus influenzae, Haemophilus parainfluenzae, Klebsiella pneumoniae, Klebsiella oxytoca, Legionella pneumophilia, Moraxella catarrhalis, Morganella morganii, Mycoplasma* spp., *Peptostreptococcus* spp., *Porphyromonas* saccharolytica, *Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes*, and *Streptococcus pyogenes*). In particular, the bacterial infection is caused by *A. baumannii* or *K. pneumoniae*. The subject may be, e.g., a human or other non-human mammal, such as a bovine, equine, canine, ovine, or feline. The non-human mammal is a bovine. The bovine may have mastitis.

The compositions described herein (e.g., a composition containing an amount (e.g., an effective antimicrobial amount) of a peptide of any one of SEQ ID NOs: 3-29, such as a peptide of SEQ ID NO: 5) may be used for treating a wound in a subject (e.g., a human or other mammal, such as a bovine, equine, canine, ovine, or feline). The wound may be, e.g., an ulcer, such as pressure sore (e.g., a bed sore) or a diabetic ulcer (e.g., a diabetic foot ulcer). The subject may be diabetic. The compositions described herein may be administered in a method to treat or reduce the severity of the wound, such as an ulcer, e.g., a diabetic foot ulcer. The compositions and methods may be used to treat a surgical site or a surgical wound. The composition can be applied to a surgical site or a surgical wound as a dressing (e.g., as a bandage or a wound dressing). The composition can be applied directly to the wound (e.g., as a liquid (e.g., a spray), an emulsion, a paste, or an ointment) or can be incorporated into or applied to a dressing and applied to the wound. The composition can be administered systemically to treat the wound.

In some embodiments, the composition may be formulated for topical administration. The composition may be administered topically to the wound, e.g., one more times daily, weekly, biweekly, or monthly. The topical administration may occur one or more times every one, two three, four, five, six, or seven days or until the wound begins to close (e.g., at the maturation phase). In certain embodiments, the topical administration occurs for 1 to 52 weeks or more (e.g., 2 weeks, 3 weeks, 4 weeks, 6 weeks, 8 weeks, 12 weeks, 24 weeks, or more).

A sixth aspect of the disclosure features a method of producing the polypeptide (e.g., an antimicrobial peptide, such as a peptide of SEQ ID NOs: 3-29, e.g., a peptide of SEQ ID NO: 5) using chemical peptide synthesis (e.g., solid phase peptide synthesis). In particular, the method of chemical peptide synthesis can feature the use of Fmoc and/or Boc synthesis.

A seventh aspect of the disclosure features a method of manufacturing the polypeptides of the first aspect by expressing the polypeptide in a cell that has been transformed with a polynucleotide of the second aspect (e.g., the polynucleotide may be present in a vector of the third aspect), and then recovering the polypeptide from the cell or the culture media surrounding the cell (e.g., an *E. coli*, or a eukaryotic cell, such as HeLa, CHO, or HEK cell).

An eighth aspect of the disclosure features a kit comprising the polypeptide of the first aspect (such as a peptide of SEQ ID NOs: 3-29, e.g., a peptide of SEQ ID NO: 5), the polynucleotide of the second aspect, the vector of the third aspect, or the composition of the fourth aspect, and, optionally, an antimicrobial agent (e.g., an antibacterial agent, such as a polymixin (e.g., colistin), or an antifungal agent). The kit component(s) can be used for the manufacture of a medicament for the treatment, prevention, or reduction in severity of a microbial infection (e.g., of a wound, such as an ulcer (e.g., a foot ulcer) in a subject (e.g., a human or other non-human mammal, such as a bovine, equine, canine, ovine, or feline).

Definitions

As used herein, the term "acidic amino acid" refers to an amino acid having a side chain containing a carboxylic acid group having a pKa between 3.5 and 4.5. Acidic amino acids are aspartic acid and glutamic acid.

The term "about" means ±10% of the stated amount.

As used herein, the term "basic amino acid" refers to an amino acid whose side chain contains an amino group having a pKa between 6.5 and 13 (e.g., between 9.5 and 13). Basic amino acids are histidine, lysine, and arginine.

The term "analog" includes any polypeptide having an amino acid residue sequence substantially identical to a polypeptide described herein in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine, or methionine for another; the substitution of one polar (hydrophilic) residue for another such as between arginine and lysine, between glutamine and asparagine, between glycine and serine; the substitution of one basic residue such as lysine, arginine, or histidine for another; and the substitution of one acidic residue, such as aspartic acid or glutamic acid for another. The phrase conservative substitution also includes the use of a chemically derivatized residue in place of a non-derivatized residue.

The term "chemical derivative" refers to a subject polypeptide having one or more amino acid residues chemically derivatized by reaction of a functional side group. Examples of such derivatized amino acids include for example, those amino acids in which free amino groups have been derivatized to form amine hydrochlorides, p-toluene sulfonyl groups, carbobenzoxy groups, t-butyloxycarbonyl groups, chloroacetyl groups or formyl groups. Also, the free carboxyl groups of amino acids may be derivatized to form salts, methyl and ethyl esters or other types of esters or hydrazides. Also, the free hydroxyl groups of certain amino acids may be derivatized to form O-acyl or O-alkyl derivatives. Also, the imidazole nitrogen of histidine may be derivatized to form N-imbenzylhistidine. Also included as chemical derivatives are those proteins or peptides which contain one or more naturally occurring amino acid derivatives of the twenty standard amino acids. For example, 4-hydroxyproline may be substituted for proline, 5-hydroxylysine may be substituted for lysine, 3-methylhistidine may be substituted for histidine, homoserine may be substituted for serine, and ornithine may be substituted for lysine. Polypeptides described herein also include any polypeptide having one or more additions and/or deletions of residues relative to the sequence of any one of the polypeptides whose sequence is described herein.

As used herein, a "coding region" is a portion of the nucleic acid which contains codons that can be translated into amino acids. Although a "stop codon" (TAG, TGA, TAA) is not translated into an amino acid, it may be considered to be part of a coding region, if present, but any flanking sequences, for example, promoters, ribosome binding sites, transcriptional terminators, introns, 5' and 3' untranslated regions, and the like, are not part of the coding region.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is, therefore, interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "duration" refers to the length of time or a time-course over which a therapeutic agent (e.g., a peptide described herein or a composition containing such a peptide, or polynucleotide encoding such a peptide) is administered.

As used herein, the term "host cell" refers to any kind of cellular system that can be engineered to generate the antimicrobial peptides (AMPs) described herein.

As used herein, the term "nonpolar amino acid" refers to an amino acid having relatively low-water solubility. Nonpolar amino acids are glycine, leucine, isoleucine, alanine, phenylalanine, methionine, tryptophan, valine, and proline.

As used herein, the term "percent (%) identity" refers to the percentage of amino acid residues of a candidate sequence that are identical to the amino acid residues of a reference sequence, e.g., an AMP disclosed herein, after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100\times(\text{fraction of } A/B)$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described above. Comparisons between two sequences are typically performed by comparing the sequences over a comparison window to identify and compare local regions of sequence similarity. A "comparison window" as used herein, refers to a segment of at least about 5 contiguous positions, about 10 contiguous positions, about 15 contiguous positions, or more, in which a sequence may be compared to a reference sequence of the same number of contiguous positions after the two sequences are optimally aligned.

As used herein, the term "pharmaceutically acceptable carrier" refers to an excipient or diluent in a pharmaceutical composition. The pharmaceutically acceptable carrier is compatible with the other ingredients of the formulation and not deleterious to the recipient. The pharmaceutically acceptable carrier may provide pharmaceutical stability to the composition (e.g., stability to an AMP), or may impart another beneficial characteristic (e.g., sustained release characteristics). The nature of the carrier may differ with the mode of administration. For example, for intravenous administration, an aqueous solution carrier is generally used; for oral administration, a solid carrier may be preferred.

As used herein, the term "pharmaceutical composition" refers to a medicinal or pharmaceutical formulation that contains an active ingredient at a pharmaceutically acceptable purity as well as one or more excipients and diluents that render the active ingredient suitable for the method of administration. The pharmaceutical composition includes pharmaceutically acceptable components that are compatible with, for example, an AMP described herein. The pharmaceutical composition may be in aqueous form, for example, for intravenous or subcutaneous administration, in tablet or capsule form, for example, for oral administration, or in cream for, for example, for topical administration.

As used herein, the term “polar amino acid” refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids are serine, threonine, cysteine, histidine, methionine, tyrosine, tryptophan, asparagine, and glutamine.

As used herein, the term “subject” refers to a mammal, e.g., a human or other non-human mammal, such as a bovine, equine, canine, ovine, or feline.

The term “sample,” as used herein, refers to a composition that is obtained or derived from a subject and/or individual of interest that contains a cellular and/or other molecular entity that is to be characterized and/or identified, for example, based on physical, biochemical, chemical, and/or physiological characteristics. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, tissue culture medium, tissue extracts such as homogenized tissue, tumor tissue, cellular extracts, and combinations thereof.

As used herein, the term “therapeutically effective amount” refers to an amount, e.g., a pharmaceutical dose of a composition described herein (e.g., a composition containing an AMP (such as a peptide of any one of SEQ ID NOs: 3-29, such as a peptide of SEQ ID NO: 5) or a nucleic acid based composition (e.g., a nucleic acid having a nucleotide sequence encoding an AMP, such as a nucleic acid encoding a peptide of any one of SEQ ID NOs: 3-29, such as a peptide of SEQ ID NO: 5)), effective in inducing a desired biological effect in a subject or subject or in treating a subject with a medical condition or disorder described herein (e.g., a microbial infection). A therapeutically effective amount may be an amount sufficient to exhibit antimicrobial activity against one or more strains of bacteria. A therapeutically effective amount may be determined using assays known in the art, such as a minimal inhibitory concentration (MIC) assay or a Kirby-Bauer disk diffusion test). It is also to be understood herein that a “therapeutically effective amount” may be interpreted as an amount giving a desired therapeutic effect, either taken in one dose or in any dosage or route, taken alone or in combination with other therapeutic agents.

As used herein, the terms “treatment” or “treating” refer to reducing or ameliorating a medical condition (e.g., a disease (e.g., sepsis) or a wound (e.g., a diabetic foot ulcer)) and/or symptoms associated therewith (e.g., a microbial infection). It will be appreciated that, although not precluded, treating a medical condition does not require that the disorder or symptoms associated therewith be completely eliminated. Reducing or decreasing the side effects of a medical condition, such as a microbial infection, or the risk or progression of the medical condition, may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement, or may be a reduction in the number of days during which the subject experiences the medical condition or associated symptoms (e.g., a reduction of 1-30 days, 2-12 months, 2-5 years, or 6-12 years).

Wherever any of the phrases “for example,” “such as,” “including” and the like are used herein, the phrase “and without limitation” is understood to follow unless explicitly stated otherwise. Similarly “an example,” “exemplary” and the like are understood to be non-limiting.

The term “substantially” used herein allows for deviations from the descriptor that do not negatively impact the intended purpose. Descriptive terms may be modified by the term “substantially” even if the word “substantially” is not explicitly recited. Therefore, for example, the phrase “wherein the lever extends vertically” means “wherein the lever extends substantially vertically” so long as a precise vertical arrangement is not necessary for the lever to perform its function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows daily images of two mice infected with *P. aeruginosa* and treated with vehicle control or D-CONGA-Q7 (SEQ ID NO: 5). FIG. 2B is a graph showing total integrated radiance from the wound bed measured daily in a mouse infected with *P. aeruginosa*. FIG. 2C is a graph showing total integrated radiance from the wound bed measured daily in MRSA infected mice. Statistical significance of the pairwise differences are shown, determined with a t-test on log values after applying the Bonferroni correction for multiple comparisons.

DETAILED DESCRIPTION

Figure 1:
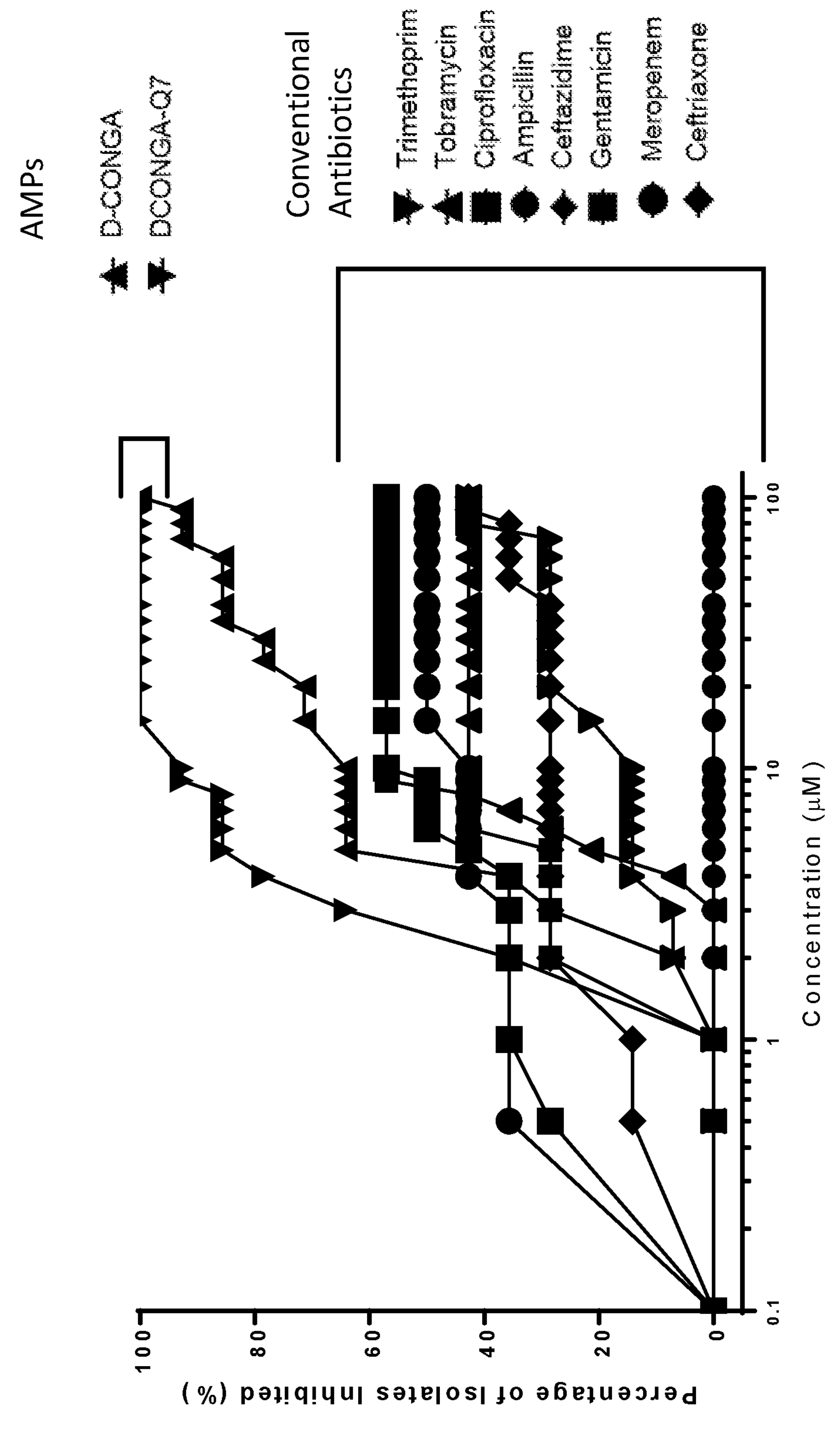
FIG. 1 is a graph showing the percentage of resistant isolates sterilized by AMPs D-CONGA (SEQ ID NO: 1) and D-CONGA-Q7 (SEQ ID NO: 5) and by conventional antibiotics. The x-axis represents the MIC in μM. The y-axis is the percentage of resistant isolates each antibiotic can eliminate in the given MIC.

Described herein are antimicrobial peptides (AMPs) capable of disrupting the cellular membrane of multiple infectious pathogens (e.g., bacterial or fungal) with improved hemocompatibility (e.g., in the presence of human red blood cells, human serum, or human tissue). We identified AMPs that retain activity against bacterial pathogens, including multi-drug resistant strains, in the presence of high concentration of red blood cells. These peptides show excellent antimicrobial activity towards a broad spectrum of bacterial species. Further, the AMPs retain this activity in the presence of eukaryotic cells and are less toxic than many previously described antimicrobial peptides. Further, the AMPs have antibiofilm activity in vitro and in vivo and are less likely to induce resistance in Gram-negative bacteria.

Antimicrobial Peptides (AMPS)

Featured are antimicrobial peptides capable of disrupting the cellular membrane of multiple pathogens with improved hemocompatibility, (e.g., in the presence of human red blood cells, human serum). For example, an AMP described herein can have at least 85% or more (e.g., 90%, 95%, 97%, 98%, 99%, or 100%) sequence identity to one or more of the sequences listed in Table 1 (e.g., SEQ ID NOs: 3-29) or any fragment thereof (e.g., fragments of at least 3, 5, 10 or more consecutive amino acids in length), in particular, the AMP has the sequence of SEQ ID NO: 5.

TABLE 1

List of AMP Sequences

| SEQ ID NO | Description | Sequence |
|---|---|---|
| 1 | D-CONGA | rrwarrlafafrr (All D) |
| 2 | L-CONGA | RRWARRLAFAFRR |
| 3 | D-CONGA-G7 | rrwarrglafafrr (All D) |
| 4 | D-CONGA-βa7 | rrwarr-βa-lafafrr (All D) |
| 5 | D-CONGA-Q7 | rrwarrqlafafrr (All D) |
| 6 | D-CONGA-ΔA4 | rrwrrlafafrr (All D) |
| 7 | D-CONGA-ΔA10 | rrwarrlaffrr (All D) |
| 8 | D-CONGA-FLIP | rrlafafwarrrr (All D) |
| 9 | D-CONGA-ΔR13 | rrwarrlafafr (All D) |
| 10 | CYCLIZED-L-CONGA-E | RRWARRLAFAFRR-E |
| 11 | CYCLIZED-L-CONGA-OH | RRWARRLAFAFRR-OH |
| 12 | D-CONGA-HomoR | rrwa (homo r, homo r)lafafrr |
| 13 | D-CONGA-NorR | rrwa (nor r, nor r)lafafrr |
| 14 | Consensus | RRW$X_1X_2X_3X_4$LAF$X_5$FR$X_6X_7$ |
| 15 | D-CONGA-L(R5,A10) | rrwaRrlafAfrr |
| 16 | L-CONGA-D(R1,R13) | rRWARRLAFAFRr |
| 17 | L-CONGA-G7 | RRWARRGLAFAFRR (All L) |
| 18 | L-CONGA-βa7 | RRWARR-βA-LAFAFRR (All L) |
| 19 | L-CONGA-Q7 | RRWARRQLAFAFRR (All L) |
| 20 | L-CONGA-ΔA4 | RRWRRLAFAFRR (All L) |
| 21 | L-CONGA-ΔA10 | RRWARRLAFFRR (All L) |
| 22 | L-CONGA-FLIP | RRLAFAFWARRRR (All L) |
| 23 | L-CONGA-ΔR13 | RRWARRLAFAFR (All L) |
| 24 | CYCLIZED-D-CONGA-E | rrwarrlafafrr-e |
| 25 | CYCLIZED-D-CONGA-OH | rrwarrlafafrr-OH |
| 26 | L-CONGA-HomoR | RRWA (homo R, homo R)LAFAFRR |

TABLE 1-continued

| List of AMP Sequences | | |
|---|---|---|
| SEQ ID NO | Description | Sequence |
| 27 | L-CONGA-NorR | RRWA (nor R, nor R)LAFAFRR |
| 28 | L-CONGA-D(R5,A10) | RRWArRLAFaFRR |
| 29 | D-CONGA-L(R1,R13) | RrwarrlafafrR |

$X_1$ is A or absent; $X_2$ and $X_3$ are each, independently, K, R, or a derivative thereof; $X_4$ is G, Q, β-A, or absent; $X_5$ is A or absent; $X_6$ is K, R, or absent, and; $X_7$ is D, E, or absent.

The featured AMPs have from about 6 to about 20 amino acids (e.g., from about 6 amino acids to about 18 amino acids, from about 6 amino acids to about 16 amino acids, from about 6 amino acids to about 14 amino acids, from about 10 amino acids to about 18 amino acids, from about 10 amino acids to about 16 amino acids, from about 12 amino acids to about 18 amino acids, or from about 12 amino acids to about 16 amino acids.

AMPs described herein can have at least 85% or more (e.g., 90%, 95%, 97%, 98%, 99%, or 100%) sequence identity to one or more of the sequences listed in Table 1 (e.g., SEQ ID NOs: 3-29) or any fragment thereof (e.g., fragments of at least 3, 5, 10 or more consecutive amino acids in length), which contain two charged residues (e.g., R or K) at the beginning and/or end of the AMP (e.g., the AMP begins with RR, RK, KR, or KK and/or ends with RR, RK, KR, or KK or any variation thereof), and may have an $AX_1AX_2$ motif, in which A is alanine and $X_1$ and $X_2$ are aromatic residues (e.g., phenylalanine, tyrosine, or tryptophan) within three amino acids (e.g., one, two or three amino acids) from the N-terminal or of the C-terminal end of the AMP.

The AMPs described herein may be substantially amphipathic. Furthermore, the AMPs may be substantially cationic and amphipathic. The AMPs may be cytostatic, cytotoxic, or both to a bacterium (e.g., Gram-positive and Gram-negative bacteria). The AMPs may also be cytostatic, cytotoxic, or both to a virus, fungus, protozoan, parasite, or a combination thereof. The AMP may be cytotoxic, cytotoxic, or both to a tumor or cancer cell (e.g., a human tumor and/or cancer cell), discriminating from normal cells based on a number of parameters, e.g., lipid composition, membrane fluidity, extent of trans-membrane electric potential, and peptides self-assembly in solution. The AMPs may be administered locally to the tumor site to facilitate tumor targeting. Alternatively, a carrier containing one or more of the AMPs (e.g., a liposome or a nanoparticle that encapsulate the AMPs) may be targeted to cancer cells using a targeting agent present on the surface of the carrier (e.g., an antibody or antigen-binding fragment thereof that specifically to a tumor-specific antigen).

The AMPs may be manufactured as a secreted peptide (e.g., for expression in a cell as a proprotein with a cleavable signal peptide). The AMPs may also be manufactured as a cyclic peptide.

The AMPs described herein may be capable of reducing an infection by a bacterial pathogen (e.g., *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium* lentum, *Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellatus, Streptococcus pneumoniae* (penicillin susceptible and resistant isolates), *Streptococcus pyogenes*, or *Streptococcus pyogenes*) and/or a fungal pathogen (e.g., from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (*e.g., Absidia* spp., *Amylomyces* spp., *Pilaira* spp., *Rhizomucor* spp., *Rhizopus* spp., or *Zygomycetes* spp.), and phylum Oomycota in the Stramenopila kingdom). For example, the AMPs described herein (e.g., a peptide of SEQ ID NO: 5) may be capable of reducing an amount of an infective bacterial and/or fungal pathogen by between about 1% and about 100% (e.g., 1%, 5%, 10%, 20%, 30%, 40%, 50%, 60%, 70%, 80%, 90%, 95%, 99%, or 100%) causing lysis of the pathogen and cell growth inhibition. The reduction may be determined in sample containing the pathogen (e.g., a blood or tissue sample). Alternatively, a physician or veterinarian may monitor the responsiveness of a subject (e.g., a human or other mammal, such as a bovine, equine, canine, ovine, or feline) to treatment (e.g., systemic and/or topical treatment) with an AMP described herein (e.g., one or more of the peptides of SEQ ID NOs: 3-29, such as a peptide of SEQ ID NO: 5) using established procedures. The responsiveness of the infecting pathogen (e.g., a bacteria or fungus) to the AMPs described herein may be monitored in vitro, wherein a sample of the pathogen is taken and grown in a laboratory setting in various concentrations of the AMP, (see, e.g., examples 3, 4, 6, and 8). Inhibition of cell growth, and the observations of the subject by a physician or veterinarian skilled in the art, can be used to indicate the responsiveness of the infection to the AMP.

Further, the AMPs described herein are capable of reducing an infection by an ESKAPE pathogen, commonly associated with antimicrobial resistance (e.g., *Enterococcus faecium, Staphylococcus aureus, Klebsiella pneumoniae, Acinetobacter baumannii, Pseudomonas aeruginosa, Enterobacter*) by between 1% and 100% (e.g., 1%, 5%, 10%, 20%, 30%, 40%, 50%, 60%, 70%, 80%, 90%, 95%, 99%, or 100%). For example, the AMPs described herein (e.g., one or more of the peptides of SEQ ID NOs: 3-29, such as a peptide of SEQ ID NO: 5) can be used to reduce an amount of an infective bacterial and/or fungal pathogen in a subject (e.g., a human or other mammal, such as a bovine, equine, canine, ovine, or feline; e.g., an amount of the pathogen present in or on the body of the subject), The reduction may be detected using, e.g., a sample from the subject containing the pathogen (e.g., a blood or tissue sample). The AMP may reduce the amount of the pathogen in the subject by between about 1% and about 100% (e.g., 1%, 5%, 10%, 20%, 30%, 40%, 50%, 60%, 70%, 80%, 90%, 95%, 99%, or 100%), e.g., by causing lysis of the pathogen and cell growth inhibition.

The AMPs described herein may be capable of reducing an infection by a fungus. The fungus may be a mold from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (*e.g., Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp., *Pilaira* spp., *Rhizomucor* spp., *Rhizopus* spp., or *Zygomycetes* spp.), and phylum Oomycota in the Stramenopila kingdom by between 1% and 100% (e.g., 1%, 5%, 10%, 20%, 30%, 40%, 50%, 60%, 70%, 80%, 90%, 95%, 99%, or 100%).

Also featured are peptidomimetics of the AMPs described herein, which include chemically modified peptides, peptide-like molecules containing non-naturally occurring amino acids, peptoids and the like. The AMP peptidomimetics retain the characteristics of antimicrobial peptides described herein, e.g., having antimicrobial activity. In particular, an AMP peptidomimetic retains the cytotoxicity and/or cytostatic properties of the peptide from which it is derived (e.g., activity against, e.g., a bacterial cell (e.g., *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium* lentum, *Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellatus, Streptococcus pneumoniae* (penicillin susceptible and resistant isolates), *Streptococcus pyogenes*, or *Streptococcus pyogenes*), or a fungus (e.g., a mold pathogen, such as one from the phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (*e.g., Absidia* spp., *Amylomyces* spp., *Pilaira* spp., *Rhizomucor* spp., *Rhizopus* spp., or *Zygomycetes* spp.), and phylum Oomycota in the Stramenopila kingdom). In addition, the AMP peptidomimetic exhibits microbial specificity in the presence of eukaryotic cells (e.g., erythrocytes). Thus, AMPs and peptidomimetics thereof exhibit low or insignificant specificity or activity against mammalian cells.

Also featured are AMPs or analogues thereof having substantially the same effect as the AMPs described herein. Such AMPs include, but are not limited to, a substitution, addition, or deletion mutant of the AMPs described herein (e.g., in which one or two amino acids of the AMPs (e.g., the AMPs of SEQ ID NOs: 3-29) are substituted with another amino acid, are deleted, or in which one or two amino acids are added to the polypeptides). Also encompassed are peptides that are substantially homologous to the polypeptides. A variety of sequence alignment software programs are available in the art to facilitate determination of homology or equivalence of any protein to a protein of the invention.

In some AMPs described herein, D-amino acids may be used instead of or in addition to L-amino acids. Glycine does not have chirality due to two hydrogens. However, all other amino acids may be D-amino acids, including D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, AND D-VAL. In particular, one or more or all of the amino acids of the AMPs may be substituted with a D-amino acid.

In some AMPs described herein, L-amino acids may be used. Glycine does not have chirality due to two hydrogens. However, all other amino acids may be L-amino acids, including L-ALA, L-ARG, L-ASN, L-ASP, L-CYS, L-GLN, L-GLU, L-HIS, L-ILE, L-LEU, L-LYS, L-MET, L-PHE, L-PRO, L-SER, L-THR, L-TRP, L-TYR, AND L-VAL. In particular, one or more or all of the amino acids of the AMPs may be substituted with a L-amino acid. In some AMPs described herein, L-amino acids may be used at certain positions and D-amino acids may be used at other specified positions.

The AMPs disclosed herein are a group of AMPs identified by their ability to permeabilize cellular membranes of pathogens (e.g., bacterial pathogens, such as *P. aeruginosa* and *E. coli*, and fungal pathogens) in the presence of excess human biological samples (e.g., red blood cells, serum) and by their specificity for pathogen cellular membranes and low cytotoxicity to mammalian cells, such as red blood cells. AMPs are attractive drug candidates because of their potent antibacterial activity and low propensity for eliciting antibiotic resistant bacterial phenotypes. Further, the AMPs described herein were rationally designed to be active against pathogens even in the presence of eukaryotic cells, and to have a specificity for bacterial pathogens over eukaryotic cells.

Polynucleotides

Also featured are polynucleotides that encode the polypeptides described herein (e.g., polypeptides with 85% (e.g., 90%, 95%, 97%, 99%, or 100%) sequence identity to one or more of the polypeptides listed in Table 1 (e.g., polypeptides of SEQ ID NOs: 3-29, such as a peptide of SEQ ID NO: 5)). The term polynucleotide is used broadly and refers to polymeric nucleotides of any length. By way of example and not limitation, the polynucleotides of the invention may have a sequence encoding all or part of an AMP (e.g., the peptides of Table 1, and peptides with at least 85% sequence identity thereto (e.g., over at least 5, 10, or more amino acids (e.g., over the entire amino acid sequence))). The polynucleotide described herein may be, for example, linear, circular, supercoiled, single-stranded, double-stranded, branched, partially double-stranded or partially single-stranded. The nucleotides of the polynucleotide may be naturally occurring nucleotides or modified nucleotides.

Polynucleotides described herein encode AMPs that maintain activity against microbial pathogens (e.g., fungal (e.g., yeast or mold), and bacterial infection) in the presence of eukaryotic cells and exhibit decreased hemolytic activity and toxicity against eukaryotic cells.

Polynucleotide sequences that encode peptide variants within 85% sequence identity to any one of SEQ ID NOs: 3-29, and exhibiting the characteristics of AMPs described herein, may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. Other similar analysis and alignment programs can be purchased from various providers, such as DNA Star's MegAlign, or the alignment programs in GeneJockey. Alternatively, sequence analysis and alignment programs can be accessed through the World Wide Web at sites such as the CMS Molecular Biology Resource at sdsc.edufResTools/cmshp.html and ExPASy Proteomics Server at www.expasy-.org. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al., *Proc. Natl. Acad. Sci.* (*USA*) 87: 2246, 1990. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

Expression Vectors

Also featured are expression vectors containing at least one polynucleotide encoding a peptide of the invention or fragment thereof (e.g., a fragment of an AMP that retains activity against pathogens (e.g., in the presence of eukaryotic cells, such as red blood cells). For example, an expression vector includes a polynucleotide encoding one or more of the peptides of Table 1 and variants thereof having at least 85% sequence identity thereto. Expression vectors are well known in the art and include, but are not limited to, viral vectors and plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), adenovirus vectors, alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system, and herpes virus.

Nonviral vectors, such as plasmids, are also well known in the art and include, but are not limited to prokaryotic and eukaryotic vectors (e.g., yeast- and bacteria-based plasmids), as well as plasmids for expression in mammalian cells. Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells, such as NSO, CHO cells, HEK and COS, and bacterial cells, such as *E. coli.*

By way of example, a vector containing a polynucleotide encoding an AMP described herein may further contain a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further include a polynucleotide sequence encoding a linker sequence. Generally, the linking sequence is positioned in the vector between the AMP-encoding polynucleotide sequence and the polynucleotide tag sequence (e.g., a purification tag sequence). Linking sequences can encode random amino acids or could contain functional sites. Examples of linking sequences containing functional sites include, but are not limited to, sequences containing the Factor Xa cleavage site, the thrombin cleavage site, and the enterokinase cleavage site.

By way of example, and not limitation, an AMP may be generated as described herein using a mammalian expression vector in a mammalian cell culture system or a bacterial expression vector in a bacterial culture system. Primers may be used to amplify the desired sequence from a template.

Methods of Manufacture

The AMPs described herein can be prepared by chemical peptide synthesis, such as by coupling different amino acids to each other through chemical conjugation. Chemical peptide synthesis is particularly suitable for the inclusion of, e.g., D-amino acids, amino acids with non-naturally occurring side chains, and natural amino acids with modified side chains, such as methylated cysteine. Chemical peptide synthesis methods are well known in the art. Peptide synthesis can be performed as solid phase peptide synthesis (SPPS) or contrary to solution phase peptide synthesis. The best known SPPS methods are tBoc and Fmoc solid phase chemistry which is amply known to the skilled person. In addition, peptides can be linked to one other to form longer peptides using a ligation strategy (chemo selective coupling of two unprotected peptide fragments) as originally described by Kent (Schnolzer & Kent (1992) *Int. J. Pept. Protein Res.* 40, 190-193) and reviewed, for example, in Tam et al (2001) *Biopolymers* 60, 194-205. This provides the potential to achieve protein synthesis beyond the scope of SPPS. Many proteins with the size of 100-300 residues have been synthesized successfully by this method. Synthetic peptides have continued to play an ever increasing role in the research fields of biochemistry, pharmacology, neurobiology, enzymology, and molecular biology because of the advances in SPPS.

For recombinant production, one or more polynucleotides encoding the AMP, or any fragment or variant or derivative thereof, can be inserted into one or more vectors for further cloning and/or expression in a host cell. Such polynucleotides may be readily isolated and sequenced using conventional procedures. For expression, a vector (e.g., an expression vector) containing one or more of the polynucleotides of the invention is provided. Methods which are well known to those skilled in the art can be used to construct expression vectors containing the coding sequence of the AMP, or any fragment or variant or derivative thereof, along with appropriate transcriptional/translational control signals. These methods include in vitro recombinant DNA techniques, synthetic techniques, and in vivo recombination/genetic recombination. See, for example, the techniques described in Maniatis et al., *Molecular Cloning: A Laboratory Manual*, Cold Spring Harbor Laboratory, N.Y. (1989); and Ausubel et al., Current Protocols in Molecular Biology, Greene Publishing Associates and Wiley Interscience, N.Y. (1989). The expression vector can be part of a plasmid, virus, or can be a nucleic acid fragment. The expression vector includes an expression cassette into which the polynucleotide encoding the AMP, or any fragment or variant or derivative thereof, (e.g., the coding region) is cloned into operable association with a promoter and or other transcription control elements. Two or more coding regions can be present in a single polynucleotide construct, e.g., on a single vector, or in separate polynucleotide constructs, e.g., on separate (different) vectors. Furthermore, any vector may contain a single coding region, or can have two or more coding regions, e.g., a vector described herein can encode one or more polypeptides, which are post- or co-translationally separated into the final polypeptide via proteolytic cleavage. In addition, a vector, polynucleotide, or nucleic acid described herein can contain heterologous coding regions, either fused or unfused to a polynucleotide encoding the AMP, or any fragment or variant or derivative thereof. Heterologous coding regions include, for example, specialized elements or motifs, such as a secretory signal peptide or heterologous functional domain. An operable association is when a coding region for a gene product, (e.g., a polypeptide), is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that polynucleic acid. The promoter may be a cell-specific promoter that directs substantial transcription of the DNA only in predetermined cells. Other transcription control elements, besides a promoter, for example, are enhancers, operators, repressors, and transcription termination signals, can be operably associated with the polynucleotide to direct cell-specific transcription. A variety of transcription control regions are known to those skilled in the art. Examples of transcription control regions, which function in vertebrate cells, such as, but not limited to, promoter enhancer segments from cytomegaloviruses (e.g., the immediate early promoter, in conjunction with intron-A), simian virus 40 (e.g., the early promoter), and retroviruses (e.g., Rous sarcoma virus). Other transcription control regions include those derived from vertebrate genes such as actin, heat shock protein, bovine growth hormone and rabbit alpha-globin, as well as other sequences capable of controlling gene expression in eukaryotic cells. Additional suitable transcription control regions include tissue-specific promoters and enhancers as well as inducible promoters (e.g., promoter inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Once an AMP, or a fragment thereof has been produced by recombinant expression, it can be purified by any method known in the art for purification of a peptide molecule, for example, by chromatography (e.g., ion exchange, affinity, and sizing column chromatography), centrifugation, differential solubility, or by any other standard technique for the purification of proteins. Further, the AMP, or a fragment thereof can be fused to heterologous polypeptide sequences described herein or otherwise known in the art to facilitate purification or to produce therapeutic peptide.

Once isolated, an AMP, or a fragment thereof can, if desired, be further purified, e.g., by high performance liquid chromatography (see, e.g., Fisher, Laboratory Techniques in Biochemistry and Molecular Biology (Work and Burdon, eds., Elsevier, 1980); the disclosure of which is incorporated herein by reference), or by gel filtration chromatography, such as on a SUPERDEX™ 75 column (Pharmacia Biotech AB, Uppsala, Sweden). Similar purification steps can be taken for and AMP, or a fragment thereof, produced through chemical peptide synthesis. Once cleaved from the resin, the isolated AMP, or a fragment thereof, may be further purified as described above.

In some instances, the AMPs described herein are cyclic AMPs. Cyclic peptides are valuable pharmaceuticals, biotechnological products, and tools for scientific research (Davies, J. S. Amino Acids, Peptides and Proteins, 34, 149-217, 2003). Cyclic peptides may have advantages over their linear relatives in that cyclic peptides sample a more constricted conformational and configurational space. (Payne et al. Curr. Org. Chem., 6, 1221-1246, 2002). Stemming from this basic property, cyclic peptides often have stronger binding constants and favorable pharmacological properties such as resistance to proteases (Fairlie, D. P.; Tyndall, J. D. A. et al. J. Med. Chem., 43, 1271-1281, 2000). Synthetic and enzymatic systems, as well as combinations of the two, can be used to produce such cyclic peptides (Davies et al. J. Peptide Sci., 9, 471-501, 2003; Hahn et al. Proc. Nat. Acad. Sci., 101, 15585-15590, 2004).

Pharmaceutical Compositions

The antimicrobial peptides and polynucleotides described herein can be prepared as compositions that contain a pharmaceutically acceptable carrier, excipient, or stabilizer known in the art (*Remington: The Science and Practice of Pharmacy* 20th Ed., 2000, Lippincott Williams and Wilkins, Ed. K. E. Hoover), in the form of a lyophilized formulation, or as an aqueous solution. Acceptable carriers, excipients, or stabilizers are non-toxic to recipients at the employed dosages and concentrations, and may include buffers such as phosphate, citrate, and other organic acids; antioxidants including ascorbic acid and methionine; preservatives (e.g., octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The compositions (e.g., when used in the methods described herein) generally include, by way of example and not limitation, an effective amount (e.g., an amount sufficient to mitigate disease, alleviate a symptom of disease and/or prevent or reduce the progression of disease) of an AMP or a fragment thereof (e.g., an AMP of Table 1), and variants thereof with at least 85% sequence identity thereto, and analogues or derivatives thereof.

For example, the compositions can be formulated to include between about 1 μg/mL and about 1 g/mL of the AMP (e.g., between 0.5 μg/mL and 300 μg/mL, 1 μg/mL and 50 μg/mL, 20 μg/mL and 120 μg/mL, 40 μg/mL and 200 μg/mL, 30 μg/mL and 150 μg/mL, 40 μg/mL and 100 μg/mL, 50 μg/mL and 80 μg/mL, or 60 μg/mL and 70 μg/mL, or 10 mg/mL and 300 mg/mL, 20 mg/mL and 120 mg/mL, 40 mg/mL and 200 mg/mL, 30 mg/mL and 150 mg/mL, 40 mg/mL and 100 mg/mL, 50 mg/mL and 80 mg/mL, or 60 mg/mL and 70 mg/mL of the AMP).

The compositions (e.g., when used in the methods described herein) generally include, by way of example and not limitation, an effective amount (e.g., an amount sufficient to mitigate infection, and/or prevent or reduce the progression of the infection) of an AMP from Table 1, or any variants thereof with at least 85% sequence identity thereto, and analogues thereof.

The pharmaceutical composition can further include an additional agent that serves to enhance and/or complement the desired effect. By way of example, to enhance the efficacy of the one or more AMPs or fragments or combinations thereof, administered as a pharmaceutical composition, the pharmaceutical composition may further contain an antimicrobial agent (such as an antibacterial agent or an antifungal agent).

For example, as used herein, an antibacterial agent can be Afenide, Amikacin, Amoxicillin, Ampicillin, Arsphenamine, Augmentin, Azithromycin, Azlocillin, Aztreonam, Bacampicillin, Bacitracin, Balofloxacin, Besifloxacin, Capreomycin, Carbacephem (loracarbef), Carbenicillin, Cefacetrile (cephacetrile), Cefaclomezine, Cefaclor, Cefadroxil (cefadroxyl), Cefalexin (cephalexin), Cefaloglycin (cephaloglycin), Cefalonium (cephalonium), Cefaloram, Cefaloridine (cephaloradine), Cefalotin (cephalothin), Cefamandole, Cefaparole, Cefapirin (cephapirin), Cefatrizine, Cefazaflur, Cefazedone, Cefazolin (cephazolin), Cefcanel, Cefcapene, Cefclidine, Cefdaloxime, Cefdinir, Cefditoren, Cefedrolor, Cefempidone, Cefepime, Cefetamet, Cefetrizole, Cefivitril, Cefixime, Cefluprenam, Cefmatilen, Cefmenoxime, Cefmepidium, Cefmetazole, Cefodizime, Cefonicid, Cefoperazone, Cefoselis, Cefotaxime, Cefotetan, Cefovecin, Cefoxazole, Cefoxitin, Cefozopran, Cefpimizole, Cefpirome, Cefpodoxime, Cefprozil (cefproxil), Cefquinome, Cefradine (cephradine), Cefrotil, Cefroxadine, Cefsumide, Ceftaroline, Ceftazidime, Ceftazidime/Avibactam, Cefteram, Ceftezole, Ceftibuten, Ceftiofur, Ceftiolene, Ceftioxide, Ceftizoxime, Ceftobiprole, Ceftriaxone, Cefuracetime, Cefuroxime, Cefuzonam, Cephalexin, Chloramphenicol, Chlorhexidine, Ciprofloxacin, Clarithromycin, Clavulanic Acid, Clinafloxacin, Clindamycin, Cloxacillin, Colimycin, Colistimethate, Colistin, Crysticillin, Cycloserine 2, Demeclocycline, Dicloxacillin, Dirithromycin, Doripenem, Doxycycline, Efprozil, Enoxacin, Ertapenem, Erythromycin, Ethambutol, Flucloxacillin, Flumequine, Fosfomycin, Furazolidone, Gatifloxacin, Geldanamycin, Gemifloxacin, Gentamicin, Glycopeptides, Grepafloxacin, Herbimycin, Imipenem, Isoniazid, Kanamycin, Levofloxacin, Lincomycin, Linezolid, Lipoglycopeptides, Lomefloxacin, Meropenem, Meticillin, Metronidazole, Mezlocillin, Minocycline, Mitomycin, Moxifloxacin, Mupirocin, Nadifloxacin, Nafcillin, Nalidixic Acid, Neomycin, Netilmicin, Nitrofurantoin, Norfloxacin, Ofloxacin, Oxacillin, Oxazolidinones, Oxolinic Acid, Oxytetracycline, Oxytetracycline, Paromomycin, Pazufloxacin, Pefloxacin, Penicillin G, Penicillin V, Pipemidic Acid, Piperacillin, Piromidic Acid, Pivampicillin, Pivmecillinam, Platensimycin, Polymyxin B, Pristinamycin, Prontosil, Prulifloxacin, Pvampicillin, Pyrazinamide, Quinupristin/dalfopristin, Rifabutin, Rifalazil, Rifampin, Rifamycin, Rifapentine, Rosoxacin, Roxithromycin, Rufloxacin, Sitafloxacin, Sparfloxacin, Spectinomycin, Spiramycin, Streptomycin, Sulbactam, Sulfacetamide, Sulfamethizole, Sulfamethoxazole, Sulfanilimide, Sulfisoxazole, Sulphonamides, Sultamicillin, Teicoplanin, Telavancin, Telithromycin, Temafloxacin, Tetracycline, Thiamphenicol, Ticarcillin, Tigecycline, Tinidazole, Tobramycin, Tosufloxacin, Trimethoprim, Trimethoprim-Sulfamethoxazole, Troleandomycin, Trovafloxacin, Tuberactinomycin, Vancomycin, Viomycin, or pharmaceutically acceptable salts thereof, or a combination thereof.

A pharmaceutical composition of AMP may include an antimicrobial agent. The antimicrobial agent may be an antifungal agent. Antifungal agents that can be used with the compositions described herein include those that are used by medical professionals in the treatment of microbial infections, such as candidiasis, including, for example, an azole (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosine, griseofulvin, haloprogin, tolnaftate, aminocandin, chlordantoin, chlorphenesin, nifuroxime, undecylenic acid, and crystal violet, and pharmaceutically acceptable salts or esters thereof.

In embodiments in which a wound (e.g., an ulcer, e.g., a diabetic foot ulcer) is treated, the pharmaceutical composition may be formulated for topical administration. Accordingly, the composition may be formulated as a paste (e.g., medicated paste), ointment, cream, powder, or the like. The composition may be prepared as a smooth, soft, moist, and/or oily preparation that may be applied topically to the skin to treat the infection. The paste or ointment may also be applied to a sterile wound dressing, such as gauze, which is then applied to the skin so the paste or ointment contacts a wound or ulcer to be treated.

A topical composition of the disclosure may be formulated as a paste or ointment which may be applied to the wound by laying the formulated paste on sterile gauze. The paste impregnated gauze may then be placed on the wound so that the medicated paste is in contact with the wound and wound edges. A topical composition of the disclosure may be formulated as a mixture of AMPs and/or antibiotics or antifungals, which may be applied or sprayed in a wound, covering the wound bed and wound edges. The volume of the topical composition will depend on the size of a wound.

Methods of Treatment

AMPs

Generally, a composition containing an AMP can be administered (e.g., intravenously) to a subject (e.g., a human patient or other mammal, such as a bovine, equine, canine, ovine, or feline in need thereof) as a medicament (e.g., for treating a medical condition (e.g., a microbial infection)). The medical condition may be, e.g., sepsis (e.g., septic shock), strep throat, meningitis, tuberculosis, tetanus, a urinary tract infection, or a digestive system disorder or food poisoning (e.g., cholera and diverticulitis). The subject may be at risk for microbial infection (e.g., sepsis) due to their age, a compromised immune system, diabetes or other autoimmune condition, kidney or liver disease, and/or admission to a health care facility (e.g., an intensive care unit or long-term health care facility), or the subject may one that has previously received an antimicrobial treatment (e.g., an antibiotic and/or a corticosteroid) that did not resolve the infection. The infection may also be one caused by a drug-resistant pathogen. The subject may be one that is experiencing severe organ problems (e.g., organ failure, such as failure of the lungs, kidney, bladder, and/or digestive system), or at a high risk of infection, such as a subject undergoing surgery, organ transplantation, and/or chemotherapy. For example, the subject may be one that is undergoing a surgery, and the AMP composition is administered to treat or reduce the risk of microbial infection pre- or post-surgery. The subject may also be treated for a different condition (e.g., cancer), and the AMP composition is administered (e.g., prophylactically) to treat or reduce the risk of microbial infection.

The subject may be a non-human mammal, such as a bovine, equine, canine, ovine, or feline. In certain particular embodiments, the subject is a bovine, e.g., a female bovine (e.g., a dairy cow). The bovine may have a microbial infection. The microbial infection, e.g., caused by a bacterium as described herein, may cause bovine mastitis, an inflammation of the udder tissue in the bovine.

For example, an AMP described herein may be administered to a subject in need thereof (e.g., a subject, such as a human of other non-human mammal (e.g., bovine, equine, canine, ovine, or feline) that has been diagnosed with a medical condition) by a variety of routes, such as local administration at or near the site affected by the medical condition (e.g., injection near a microbial infection), intravenous, parenteral, intradermal, transdermal, intramuscular, intranasal, subcutaneous, percutaneous, intratracheal, intraperitoneal, intraarterial, intravascular, inhalation, perfusion, lavage, topical, and oral administration. The most suitable route for administration in any given case may depend on the particular AMP or composition administered, the subject, pharmaceutical formulation methods, administration methods (e.g., administration time and administration route), the subjects age, body weight, sex, severity of the medical condition (e.g., severity of the microbial infection), the subject's diet, and the subject's excretion rate. Compositions may be administered once, or more than once (e.g., once annually, twice annually, the times annually, bi-monthly, monthly, bi-weekly, weekly, daily, or more than once daily). For local administration, AMPs may be administered by any means that places the AMP in a desired location, including catheter, syringe, shunt, stent, microcatheter, pump, implantation with a device, or implantation with a scaffold.

The methods described herein may involve coordinated administration of (i) an AMP, and (ii) an antimicrobial agent (e.g., an agent which treats fungal, (e.g., yeast, or mold) or bacterial infection). The AMP and antibacterial agent are generally as described elsewhere herein, but can be, as examples, an AMP described herein (e.g., an AMP of any one of SEQ ID NOs: 3-29), and/or variants thereof, and colistin.

There are many different approaches to coordinated administration of an AMP and an antimicrobial agent that can be used in the intervention of infection. For instance, the method may include treatment with an antimicrobial agent prior to AMP administration. Taking this approach facilitates treatment of an acute episode quickly with the antimicrobial agent, while supplementing the action of the antimicrobial agent with the AMP in addressing the acute attack.

In one example, a subject is treated with an antimicrobial agent 1-4 (e.g., 2-3) times before AMP administration, and the antimicrobial treatment takes place, for example, within a time frame of 1, 2, or 3 weeks prior to AMP administration. Thus, in a specific example, a treatment with an antimicrobial agent can be carried out on days −14, −11, and −8 relative to day 0, which is the day on which administration of the AMP takes place. Any of the antimicrobial treatment and/or AMP treatment can vary (e.g., 1 or 2 days) before or after the days noted above.

In another example, antimicrobial treatment takes place concurrently with AMP administration, in addition to (or instead of) prior antimicrobial treatment according to, for example, a schedule as noted above. Thus, in one specific example, antimicrobial treatment takes place on days −14, −11, and −8 (±1 or 2 days for each day of administration), and also on day 0, the same day as AMP administration. The simultaneous treatment with an antimicrobial agent and an AMP described herein, can continue, and be monitored by one skilled in the art, until effective treatment of the infection.

The AMP described herein may be used for a treatment of an infection after the treatment with traditional antimicrobials has failed.

Compositions as described herein can be delivered to a mammalian subject (e.g., a human or other mammal) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using conventional methods, such as a syringe, or using a liquid jet injection system. Compositions can also be administered topically to skin or mucosal tissue, such as nasally, intratracheally, intestinal, rectally, or vaginally, or provided as a finely divided spray suitable for respiratory or pulmonary administration. Other modes of administration include oral administration, suppositories, and active or passive transdermal delivery techniques.

The compositions described herein can be administered to a subject (e.g., a human subject or other mammal, such as a bovine, equine, canine, ovine, or feline, that has or is at risk of developing a microbial infection) in an amount that is compatible with the dosage formulation and that will be prophylactically and/or therapeutically effective. An appropriate effective amount will fall in a relatively broad range but can be readily determined by one of skill in the art by routine trials. The "Physician's Desk Reference" and "Goodman and Gilman's The Pharmacological Basis of Therapies" are useful for the purpose of determining the amount needed. An adequate dose of the active antimicrobial agents described herein may vary depending on such factors as preparation method, administration method, severity of symptoms, administration time, administration route, rate of excretion, and responsivity. Generally, the antimicrobial agent will be administered according to the label approved by the relevant regulatory authority. An adequate dose of the AMPs described herein may vary depending on the administration route, age of the subject, the severity of infection, and the identity of the infecting pathogen. A physician or veterinarian of ordinary skill in the art can determine the administration dose effective for treatment.

Wound Healing

The compositions described herein (e.g., a composition containing an AMP of any one of SEQ ID NOs: 3-29, such as an AMP of SEQ ID NO: 5, and/or variants thereof) can be administered to a subject in need thereof to treat (e.g., to heal), or to reduce or prevent the development of, wounds or ulcers. The compositions described herein may be formulated as a topical composition to treat skin wounds and external ulcers, such as pressure ulcers, bed sores (e.g., decubitus), foot ulcers, diabetic foot ulcers, surgical wounds, and ulcers caused by gas gangrene.

Topical compositions of the disclosure, and methods of treatment, as disclosed herein, may be used to treat diabetic wounds or diabetic ulcers. For example, the topical compositions and methods of treatment disclosed herein may be used to treat diabetic ulcers that are inflamed or infected. In some cases, the topical compositions and methods of treatment disclosed herein may be used to prevent or treat infection of a wound or an ulcer. For example, topical compositions and methods of treatment disclosed herein may be used to prevent or treat an infection of an ulcer or wound caused by bacteria or fungi as described herein. In certain embodiments, the methods are used to treat a wound or ulcer caused by, e.g., *Staphylococcus* (e.g., *Staphylococcus aureus*, e.g., methicillin-resistant *Staphylococcus aureus* (MRSA)), *Streptococcus*, and/or *Pseudomonas* (e.g., *Pseudomonas aeruginosa*).

In other examples, the topical compositions and methods of treatment disclosed herein may prevent or reduce the need for surgical debridement or amputation. Topical compositions and methods of treatment disclosed herein may be used to heal ulceration due to, e.g., an autoimmune condition, such diabetes and systemic lupus erythematosus. Topical compositions and methods of treatment disclosed herein may be used to heal ulceration caused by, for example, gas gangrene. In many examples, the topical compositions and methods of treatment disclosed herein may reduce the time of treatment and increase the healing time, as compared with other methods of wound healing known in the art.

The topical compositions may be applied prior to or after a surgical operation (e.g., at a surgical site), in order to treat or reduce the risk of infection by a pathogen.

In some embodiments, the methods described herein reduce the size of a wound or ulcer, e.g., by at least 5%, 10%, 15%, 20%, 25%, 30%, 40%, 50%, 60%, 70%, 80%, 90%, 95%, 97%, 99%, or 100%, e.g., relative to the original size of the wound or ulcer.

Dosage and Administration

The pharmaceutical compositions described herein can be administered to a subject (e.g., a human or other mammal, such as a bovine, equine, canine, ovine, or feline) in a variety of ways. For example, the pharmaceutical compositions may be formulated for and/or administered orally, buccally, sublingually, parenterally, intravenously, subcutaneously, intramedullary, intranasally, as a suppository, using a flash formulation, topically, intradermally, subcutaneously, via pulmonary delivery, via intra-arterial injection, ophthalmically, optically, intrathecally, or via a mucosal route.

In general, the dosage of a pharmaceutical composition or the active agent (e.g., an AMP described herein, such as an AMP of any one of SEQ ID NOs: 3-29, e.g., an AMP of SEQ ID NO: 5, and/or variants thereof) in a pharmaceutical composition described herein may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g, 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 μg, e.g., 200 ng, 300 ng, 400 ng, 500 ng, 600 ng, 700 ng, 800 ng, 900 ng, 1 μg, e.g., 1-10 μg, e.g., 1 μg, 2 μg, 3 μg, 4 μg, 5 μg, 6 μg, 7 μg, 8 μg, 9 μg, 10 μg, e.g., 10 μg-100 μg, e.g., 20 μg, 30 μg, 40 μg, 50 μg, 60 μg, 70 μg, 80 μg, 90 μg, 100 μg, e.g., 100 μg-1 mg, e.g., 200 μg, 300 μg, 400 μg, 500 μg, 600 μg, 700 μg, 800 μg, 900 μg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g). For example, the AMP may be administered in any of the amounts described above at a volume in the range of 1 μL to 500 mL (e.g., 1-10 μL, e.g., 1 μL, 2 μL, 3 μL, 4 μL, 5 μL, 6 μL, 7 μL, 8 μL, 9 μL, 10 μL, e.g., 10 μL-100 μL, e.g., 20 μL, 30 μL, 40 μL, 50 μL, 60 μL, 70 μL, 80 μL, 90 μL, 100 μL, e.g., 100 μL-1 mL, e.g., 200 μL, 300 μL, 400 μL, 500 μL, 600 μL, 700 μL, 800 μL, 900 μL, 1 mL, e.g., 1 mL-10 mL, e.g., 2 mL, 3 mL, 4 mL, 5 mL, 6 mL, 7 mL, 8 mL, 9 mL, 10 mL, 10 mL-100 mL, e.g., 20 mL, 30 mL, 40 mL, 50 mL, 60 mL, 70 mL, 80 mL, 90 mL, 100 mL, e.g., 100 mL-500 mL, e.g., 200 mL, 300 mL, 400 mL, 500 mL).

The pharmaceutical composition may also be administered in a unit dose form or as a dose per mass or weight of the subject from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the subject per unit day (e.g., 0.1-10 mg/kg/day).

The dosage regimen may be determined by the clinical indication being addressed, as well as by various subject variables (e.g., weight, age, sex) and clinical presentation (e.g., extent or severity of disease). Furthermore, the pharmaceutical compositions may be administered continuously or divided into dosages given per a given time frame. The composition may be administered (e.g., systemically) or applied (e.g., to a wound site), for example, one or more times every hour, day, week, month, or year.

In embodiments in which a wound (e.g., an ulcer, e.g., a diabetic foot ulcer) is treated, the composition may be formulated for topical administration. The composition may be administered topically to the wound one or more times daily, weekly, biweekly, or monthly. The topical administration may occur one or more times every one, two, three, four, five, six, or seven days. The topical administration may occur from 1 to 52 weeks or more (e.g., 2 weeks, 3 weeks, 4 weeks, 6 weeks, 8 weeks, 12 weeks, 24 weeks, or more).

Kits

AMPs

Also featured are kits containing an AMP described herein (e.g., an AMP of any one of SEQ ID NOs: 3-29, such as an AMP of SEQ ID NO: 5, and/or variants thereof), e.g., for use in the instant methods. Kits of the invention include one or more containers comprising, for example, AMPs, polynucleotides encoding one or more AMPs, combinations thereof, and fragments thereof, and, optionally, instructions for use in accordance with any of the methods described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also envisioned The kits may be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g., the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

The kit may also include the composition formulated for topical administration (e.g., as a paste (e.g., medicated paste), ointment, cream, powder, or the like). The composition may be present in the kit in a tube, spray bottle, jar, or other container.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1. AMP Synthesis

AMPs are synthesized using solid phase peptide synthesis on TentaGel-S-ram resin. Coupling of FMOC-protected amino acids was catalyzed by HBTU (2-(1H-benzotriazol-1-yl)-1,1,3,3-tetramethyluronium hexafluorophosphate, Hexafluorophosphate Benzotriazole Tetramethyl Uronium), HOBt (hydroxym, benzotriazole), and DIPEA (diisopropylethylamine). After coupling, FMOC was removed by piperidine in dimethylformamide. Cleavage of side chain protecting groups and release of peptide from the resin was done with trifluoroacetic acid containing water, phenol and triisopropylsilane. Purification was by reverse phase high pressure liquid chromatography. Cyclization was done by direct coupling of the N-terminal amino group to either a C-terminal carboxyl group (CONGA-OH) or to the side-chain of a C-terminal glutamate-amide (CONGA-E). Coupling was done using standard peptide synthesis coupling reagents.

Example 2. AMP Variants Retain Activity

Peptide variants of D-CONGA (SEQ ID NO: 1) were tested for activity against *E. coli*, *K. pneumoniae*, and *S. aureus*. Minimum Inhibitory Concentrations (MIC) were measured in 96-well plates by broth dilution. Peptides were serially diluted in buffer or in buffer containing $1\times10^9$ human RBC/ml. Following 1 hr. incubation, bacteria in growth media were added and the plates were incubated overnight at 37 °C. Sterilized, wells were identified to determine MIC. Hemolysis was measured by incubating $1\times10^8$ human RBCs with serially diluted peptide for 30 minutes followed by centrifugation of the cells and measurements of the released hemoglobin in the supernatant by absorbance at 410 nm. The value for 100% hemolysis was established by treatment with the detergent Triton™ X100. Toxicity was measured by incubating serially diluted peptide with WI38 human fibroblast cells in the presence of SYTOX™ Green, a DNA binding dye that reports on cell death by membrane permeabilization. The peptide concentration that gives 50% cytotoxicity by relative SYTOX™ Green fluorescence, is denoted EC50.

Data showing MIC values in the absence and presence of concentrated human RBCs, hemolysis by 100 micromolar peptide, and the $EC_{50}$ for toxicity against human fibroblast cells (WI-38 Cell) are provided in Table 2. These data show that peptide variants of D-CONGA (SEQ ID NO: 1) retain activity against clinically relevant infectious pathogens (e.g., *E. coli, K. pneumoniae*, and *S. aureus*) in the presence of concentrated host cells.

TABLE 2

| | | | *E. coli* | | *K. pneumoniae* | | *S. aureus* | | |
|---|---|---|---|---|---|---|---|---|---|
| | | | MIC, µM | | | | | | |
| Peptide | Sequence | Hemolysis at 100 µM | No RBC | $10^9$ cells/ml RBC | No RBC | $10^9$ cells/ml RBC | No RBC | $10^9$ cells/ml RBC | EC50, µM (WI-38 Cells) |
| D-CONGA | rrwarrlafafrr (SEQ ID NO: 1) | 0.06 | 1.0 | 0.8 | 4.4 | 3.8 | 5.7 | 6.3 | 110 |
| D-CONGA-G7 | rrwarrglafafrr (SEQ ID NO: 3) | 0.07 | 1.3 | 1.4 | 1.7 | 4.7 | 6.4 | 6.9 | 235 |
| D-CONGA-βa7 | rrwarr-βa-lafafrr (SEQ ID NO: 4) | 0.02 | 1 | 1.3 | 1.4 | 1.5 | 30 | 30 | 6160 |
| D-CONGA-Q7 | rrwarrqlafafrr (SEQ ID NO: 5) | 0.07 | 1 | 1.7 | 1.1 | 1.5 | 4.2 | 3.6 | 418 |
| D-CONGA-ΔA4 | rrwrrlafafrr (SEQ ID NO: 6) | 0.02 | 1.6 | 2.8 | 4.5 | 6.2 | 3.2 | 2.3 | 143 |
| D-CONGA-ΔA10 | rrwarrlaffrr (SEQ ID NO: 7) | 0.02 | 0.7 | 1.3 | 1.6 | 30 | 24 | 19 | 257 |
| D-CONGA-FLIP | rrlafafwarrrr (SEQ ID NO: 8) | 0.05 | 1 | 1.5 | 1.2 | 1.4 | 1.7 | 3.7 | 143 |
| D-CONGA-ΔR13 | rrwarrlafafr (SEQ ID NO: 9) | 0.03 | 0.9 | 0.6 | 2.1 | 2.1 | 27 | 30 | >500 |
| D-CONGA-L(R5, A10) | rrwaRrlafAfrr (SEQ ID NO: 15) | 0.04 | 1.4 | 1.4 | 2.3 | 2.2 | 30 | 30 | 2500 |
| L-CONGA-D(R1, R13) | rRWARRLAFAFRr (SEQ ID NO: 16) | 0.01 | 20 | 26.2 | 5.1 | 9.3 | 30 | 30 | 134 |
| CYCLIZED-L-CONGA-E | RRWARRLAFAFRR-E (SEQ ID NO: 10) | 0.03 | 24 | 30 | 20 | 30 | 30 | ND | ND |
| CYCLIZED-L-CONGA-OH | RRWARRLAFAFRR-OH (SEQ ID NO: 11) | 0.7 | 5.9 | 13.3 | 2.9 | 5.9 | 20 | ND | ND |
| D-CONGA-HomoR | rrwa (homo r, homo r)lafafrr (SEQ ID NO: 12) | 0.06 | 1.3 | 2.2 | 8.0 | 5.4 | 1.7 | 2.5 | 143 |
| D-CONGA-NorR | rrwa (nor r, nor r)lafafrr (SEQ ID NO: 13) | 0.03 | 1.9 | 2.4 | 13 | 12 | 7.6 | 17.2 | 66 |

Example 3. Minimum Sterilizing Concentration of AMPs in the Presence of RBCs To determine the lowest concentration of AMP (e.g., an AMP of the disclosure (e.g., an AMP of any one of SEQ ID NOs: 3-29)) that is capable of effectively limiting bacterial growth in the presence of RBCs, a modified Broth Dilution assay can be performed. AMPs of the disclosure (e.g., any one of SEQ ID NOs: 3-29) and small molecule antibiotics (e.g., vancomycin and streptomycin) can be prepared at 5-times the final concentration needed in 0.025% acetic acid in $H_2O$. The AMPs and antibiotics can be serially diluted by a factor of 2:3 horizontally across a 96-well, canonical-bottomed plate, 25 µL per well. One column can be reserved for controls. RBCs at 0 and $2.5\times10^9$ cells/mL can be added in 50 µL aliquots to the appropriate wells. Following a 30-minute incubation, 50 µL of TSB growth media, inoculated with $5\times10^5$ CFU/mL, can be added to all wells, and plates can be incubated overnight at 37 °C. To assess bacterial growth, a second inoculation of the AMP and small molecule antibiotic can be performed with 10 µL of solution from the original plate added to 100 µL of sterile TSB.

Following overnight incubation at 37 °C, the OD600 can be measured (values of less than 0.1 were considered sterilized).

Example 4. Radial Diffusion in the Presence of RBCs

To further determine the activity of an AMP (e.g., an AMP of the disclosure (e.g., an AMP of any one of SEQ ID NOs: 3-29)) in the presence of RBCs, a modified radial diffusion assay can be performed. AMPs can be introduced to a small well in an agarose plate and can be allowed to diffuse into the surrounding medium. The plate, which can be seeded with bacterial cells, can be incubated overnight and the extent of microbial growth can be examined and, if the AMP was effective, a small zone of growth inhibition can be apparent around the well. Underlay agarose can be prepared by adding 5 g of low EEO agarose and 0.03 g of TSB to 500 mL of 10 mM phosphate buffer (pH=7.4). Overlay agarose can be prepared by adding 5 g of low EEO agarose and 30 g of TSB to 500 mL of 10 mM phosphate buffer (pH=7.4). Both solutions can be heated until the agarose melted and then can be autoclaved. To a rectangular, one-well plate, 20 mL of underlay agarose, inoculated with $8\times10^6$ CFUs of bacteria, can be added. A sterile, 96-well plate replicator from Sigma-Aldrich can be set in the molten agarose and removed once the agarose solidified. Antibiotic (e.g., vancomycin and streptomycin) can be prepared at 4 times the final desired concentration. For the antibiotic standard, a serial dilution of 3:4 across a 96-well plate is performed followed by 1:4 dilution with PBS. Otherwise, the AMP can be diluted to 20 μM with RBCs and/or serum to give between 2% ($1\times10^8$ cells/mL) and 20% ($1\times10^9$ cells/mL). Solutions are incubated with gentle shaking for 30 minutes at 37 °C, prior to the addition of 10 μL of AMP or small molecule antibiotic to the wells in the underlay. Inverted plates were incubated at 37 °C for 3 hours. Overlay is added, and the plate can be incubated upside down overnight. Surface growth can be cleared, the plates can be sterilized with 25% methanol and 5% acetic acid. The ability of the AMP to inhibit bacterial growth can be assessed by analyzing zones of inhibition, which can be photographed and analyzed using ImageJ.

Example 5. Hemolysis Assay

The destruction of a large number of blood cells, in vivo, can be problematic for the host, leading to conditions such as anemia and jaundice, thus it is important to measure hemolysis of potential therapeutics in vitro. An AMP of the disclosure (e.g., an AMP of any one of SEQ ID NOs: 3-29) can be serially diluted in PBS starting at a concentration of 100 μM. The final volume of each AMP in each well can be 50 μL. To each well, 50 μL of RBCs in PBS at $2\times10^8$ cells/mL can be added. As a positive lysis control, 1% TRITON™ can be used. The mixtures can be incubated at 37 °C for 1 hour, after which they can be centrifuged at 1000×g for 5 minutes. After centrifugation, 10 μL of supernatant can be transferred to 90 μL of DI $H_2O$ in a fresh 96-well plate. The absorbance of released hemoglobin at 410 nm can be recorded and the fractional hemolysis can be calculated based on the 100% and 0% lysis controls to identify the potential toxicity of the AMP. A larger fractional hemolysis score indicates a higher hemolytic toxicity.

Example 6. CFU Reduction Assay

To gain a better understanding of the behavior of AMPs in the presence of RBCs, a modified colony forming unit (CFU) reduction assay having RBCs can be performed. Unlike a broth dilution assay which observes all-or-nothing growth/sterilization, the CFU assay observes the number of viable bacterial cells remaining in suspension after a fixed incubation period with an AMP (e.g., an AMP of any of SEQ ID NOs: 3-29). CFU reduction by AMPs can be calculated by plating and counting CFUs in dilutions of the mixtures. An AMP can be prepared at 5× the final concentration in 0.025% acetic acid and 30 μL can be added to a single well of a 96-well plate. A bacterial suspension can be prepared in PBS at $2.5\times10^9$ cells/mL. PBS or RBCs at $2.5\times10^9$ cells/mL can be added to peptide in a volume of 60 μL. The plates can be then incubated at 37 °C for 1 hour. The mixtures can then be serially diluted 1:10 and the dilutions can be spotted on TSB agar. The agar plates can be incubated at 37 °C overnight and colonies can be counted the next day to determine the efficacy of the AMPs in the presence and absence of RBCs.

Example 7. Peptide Extraction

Beads can be affixed to petri dishes by adding a small amount of methanol to a pool of resin beads and allowing it to evaporate. The beads can be "pre-cleaved" by exposure to UV light for five hours. Prior to use in an antimicrobial assay(s), 30 μL of 0.025% acetic acid can be added to each well of a 96-well plate. Individual beads can be picked from the petri dish using forceps and placed in a well (one bead per well). To each well, 30 μL of HFIP can be added, and the plate can be incubated under UV-light with shaking for 2 hours (or until the solvent evaporated). Next, 35 μL of PBS can be added to all wells and the plates can be placed on a shaker overnight. Prior to an assay, the peptide solutions can be transferred to a fresh 96-well plate to separate peptide solution from synthesis resin and the extraction plates can be stored for indexing. The average concentration of extracted peptide can be ~15 μM.

Example 8. Mixed Radial Diffusion Broth Dilution Screen

A mixed radial diffusion broth dilution screen highlights the benefits of a broth dilution assay and a radial diffusion assay (Examples 3 and 4, respectively). To 30 μL of extracted peptide in a 96-well plate, 6 μL of RBCs at $6\times10^9$ cells/mL can be added and the plates can be incubated for 1 hour with shaking at room temperature. Following incubation, the plates can be centrifuged at 1000×g for five minutes to pellet the cells. Five microliters of supernatant can be removed from the plate and added to 60 μL of PBS in a second plate. This plate can be read at 410 nm for hemolysis. Next, the cells can be resuspended and 10 μL of the solution can be added to a radial diffusion plate harboring *E. coli*. These plates can be processed as described above in Example 4. To the remaining 20 μL of peptide/RBC solution, 20 μL of *P. aeruginosa* at $5\times10^5$ CFU/mL in 1% TSB in PBS can be added. The plate can be allowed to incubate for 3 hours at 37 °C. Following incubation, 40 μL of 2×TSB can be added and the plate can be incubated at 37 °C overnight. Because of the presence of dense RBCs, inhibition of bacterially growth can be initially detected by a lack of deoxygenation in the wells (as evidenced by RBC coloration). Wells that are suspected to have been inhibited can have an aliquot removed and spread on a TSA plate. These plates can be incubated at 37 °C to verify the presence/absence of microbes.

Example 9. Cytotoxicity Assay(s)

AMPs described herein (e.g., an AMP of any one of SEQ ID NOs: 3-29) can be tested for toxicity towards mammalian cells, e.g., human cells. Epithelial liver cancer cells, e.g., CCLP-1 cells, can be grown to confluency in T-75 flasks in complete DMEM (10% FBS). The day prior to cytotoxicity experiments, cells can be trypsinized, removed from the flask, and pelleted at 1000×g. The trypsin and spent media can be discarded and the cells can be resuspended in complete DMEM. The cell count can be obtained using a standard hemocytometer. The cells can then be seeded at a density of 3.5×104 cells/well in a 96-well tissue-culture plate. In a separate 96-well plate, AMP (e.g., an AMP of the disclosure (e.g., an AMP of any one of SEQ ID NOs: 3-29)) can be serially diluted in serum-free DMEM starting at a concentration of 100 μM. The final volume of peptide in each well can be 100 μL. To perform the cytotoxicity assay, media can be removed from the wells and replaced with the peptide/DMEM solutions. No peptide, AMPs of SEQ ID NOs: 1 and 2 and 20 μM melittin in serum-free media can be used as negative and positive controls, respectively. The cells can be incubated for one hour in a standard tissue-culture incubator. After this incubation, 10 μL of ALAMAR-BLUE® assay reagent can be added to each well in the plate and the plate can be returned to the incubator. After two hours of additional incubation, the plate can be read for fluorescence with an excitation wavelength of 530 nm and an emission wavelength of 590 nm. The cytotoxicity can be calculated based on the 100% and 0% lysis controls.

Example 10. Treating an Infection Using an AMP

A subject having an infection by a pathogen (e.g., *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium lentum, Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellatus, Streptococcus pneumoniae* (penicillin susceptible and resistant isolates), *Streptococcus pyogenes*, or *Streptococcus pyogenes*) can be treated using an AMP (e.g., an AMP of any one of SEQ ID NOS: 3-29). If the infection is in a wound, the AMP (e.g., an AMP of any one of SEQ ID NOs: 3-29, such as an AMP of SEQ ID NO: 5, and/or variants thereof) could be administered in a proper formulation (e.g., dissolved in a buffer, or incorporated into a cream or other topical composition). Following administration, the AMPs target and lyse the microbial cells, thereby inhibiting growth and treating the infection. Following administration of the AMP, a practitioner skilled in the art can monitor the subject's improvement in response to the AMP therapy by a variety of methods.

Example 11. Preventing an Infection in an Immunocompromised Subject

An immunocompromised subject (e.g., a subject having cancer, undergoing chemotherapy) can, after surgery, be treated with an antimicrobial peptide described herein (e.g., SEQ ID NOs: 3-29) to treat infection and/or inhibit the growth of the pathogen (e.g., *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordeffii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium lentum, Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellatus, Streptococcus pneumoniae* (penicillin susceptible and resistant isolates), *Streptococcus pyogenes*, or *Streptococcus pyogenes*) including drug resistant forms (e.g., methicillin resistant *S. aureus* and vancomycin resistant *Enterococcus*), thereby treating and/or protecting the subject from the infection.

Example 12. Sterilizing a Surface Using an AMP

A surface (e.g., an operating table or tool bench) can be sterilized to remove pathogens (e.g., methicillin resistant *S. aureus*) by the application of a suitable composition containing an AMP described herein (SEQ ID NOs: 3-29) for a suitable duration. Multi-drug resistant pathogens are becoming increasingly common in the hospital environment and are a growing problem. AMPs, with their low propensity for eliciting antibiotic resistant bacterial phenotypes can be used to sterilize hospital surfaces of microbial pathogens (e.g., bacteria or fungus) including multi-drug resistant pathogens (e.g., methicillin resistant *S. aureus*).

Example 13. Testing AMPs for Induction of Resistance

Bacterial resistance against peptide antibiotics is known to occur, although it is reportedly more difficult to induce than resistance against conventional small molecule antibiotics. *P. aeruginosa* can gain resistance to some AMPs through selection for a variant with altered outer membrane composition. *P. aeruginosa* can be used in a screen to select against rapid resistance. AMPs of the disclosure (e.g., an AMP of any one of SEQ ID NOs: 3-29) can be tested to determine if they avoid producing *P. aeruginosa* resistance to the AMPs described herein and may be compared to *P. aeruginosa*'s ability to adapt to conventional antibiotics (e.g., small molecule antibiotics) under the same conditions. For ten serial passages, broth sterilization assays can be performed using ⅔ serially diluted antibiotics with overnight growth. For each passage, the bacteria that grew at the highest antibiotic concentration can be used to expand overnight for the subsequent generation.

Example 14. Testing AMPs for Treatment of Wound Microbial Infection

Deep wounds in mice can be infected with a luminescent strain of *P. aeruginosa* and monitored with whole animal imaging. Treatment can be twice per day, with AMP (e.g., an AMP of the disclosure (e.g., an AMP of any one of SEQ ID NOs: 3-29)) in a suitable vehicle (e.g., 0.025% acetic acid) starting 2 hours after infection. The AMP D-CONGA and L-CONGA (SEQ ID NOs: 1 and 2, respectively) can be used as positive controls. Animals can be treated on days 0, 1, and 2. The treated mice can be monitored for summed behavioral scores (behavioral scores scale is 0 (normal) to 3 (maximally abnormal) each for activity/nesting, movement, grip strength, coat condition, and posture, to determine the efficacy of AMP treatments. Maximum score (worst condition) =15).

Example 15. Treatment of Acute Pneumonia Induced by *P. aeruginosa* Aspiration with AMPs Female C57BL/6 mice, aged five weeks, can be obtained from Charles River Laboratories. Upon receipt, they can be allowed at least one week to recover from transport and acclimate to the new housing environment. Mice can be maintained on a standard chow diet. Experiments can be performed with mice no younger than six weeks and no older than nine weeks. *P. aeruginosa* PA01 can be cultured overnight in tryptic soy broth (TSB) at 37 °C and shaken at 220 RPM. Prior to infecting the mice, the overnight culture can be diluted 100-fold into 25-mL of fresh TSB. The culture can be grown for three hours before optical density can be determined. Previous growth curve experiments can allow for the dilution of this newly expanded culture to $1.4\times10^8$ CFU/mL. To infect an animal, mice can be anesthetized using isoflurane and 50 µL of bacterial suspension ($7\times10^6$ CFUs) can be administered via intratracheal instillation. Briefly, the anesthetized mice can be suspended from wire by their front feet and blunt forceps can be used to extract the tongue. The tongue can be pulled out and downward. The bacterial suspension can be deposited in the back of the throat with a micropipette. The nares of the animal can then be covered while the mouse recovered from anesthesia. The chest can be gently rubbed to promote inhalation. The mice can be made to inhale 15 times before the tongue can be released and the mouse can be removed from the wire. The animals can then be allowed a minute to fully awaken and then returned to their cages.

The mice can then be treated with an AMP described herein (e.g., an AMP of any one of SEQ ID NOs: 3-29), and the AMP D-CONGA (SEQ ID NO: 1) and L-CONGA (SEQ ID NO: 2) can be used as positive controls, which can be instilled in the trachea, exactly as described above for the administration of bacterial infection. Before attempting to treat a *P. aeruginosa* infection of the lung, one can establish a safe dose for administration of the AMP via aspiration. Based on in vitro toxicity data, a dosing regimen of can be, for example, administered every 8 hours for 3 days (9 doses). As a no treatment control, an equal volume of PBS can be administered on the same schedule.

To monitor the toxicity, animal behavior and body weight changes can be measured. These studies can show the mice can be able to tolerate an oral dose of the AMPs.

Example 16

We identified AMPs, such as D-CONGA, that were highly effective in vitro against all ESKAPE pathogens in the presence of RBCs and serum. The peptide also has anti-biofilms activity in gram-positive and gram-negative bacteria and shows potency against gram-negative and gram-positive drug-resistant bacteria and their biofilms in an infected wound model in mice.

Here, we synthesized 13 variants of D-CONGA, which can be broadly divided into 4 classes, insertions, deletions, swaps, and cyclized. These variants were then characterized for their activity against gram-positive *S. aureus* and gram-negative *E. coli* and *K. pneumonia* in the presence and absence of RBCs. Their cytotoxicity against mammalian fibroblast, WI-38, and hemolysis in RBC was also measured. The best variant AMP was then tested against 14 clinical isolates that included resistant strains of *K. pneumonia*, PDR *A. baumannii*, methicillin-resistant *S. aureus* and *P. aeruginosa* from patients with cystic fibrosis. The antimicrobial activities of the peptide were compared with D-CONGA and eight conventional antibiotics from four different classes. We have identified AMPs that exhibit improved activity against MDR bacterial strains relative to conventional antibiotics.

Methods and Materials

Peptides and Antibiotics.

Peptides were either synthesized in the lab using solid-phase peptide synthesis (SPSS) method or were obtained from Bio-Synthesis Inc. (Lewisville, Texas). They had purities >95% by HPLC. Antibiotics were obtained from various vendors. Unless otherwise stated, all solutions were prepared by dissolving lyophilized peptide or antibiotic powders in 0.025% v/v) acetic acid and concentrations were determined by absorbance at 280 nm.

Broth Dilution Assay.

Antimicrobial peptides and conventional antibiotics were prepared at 5-times the final concentration needed in 0.025% acetic acid. The antibiotics were serially diluted by a factor of 2:3 horizontally across 96-well plates from Corning, 25 μL per well. One column was reserved for controls. For the assays performed in the presence of RBC, type O+ human RBCs at 0 or $2.5\times10^9$ cells/mL were added in 50 μL aliquots to all wells. Following a 30-minute incubation, 50 μL of TSB, inoculated with $5\times10^5$ CFU/mL, was added to all wells, and plates were incubated overnight at 37 °C. Following overnight incubation at 37 °C, the OD600 was measured (values of less than 0.1 were considered sterilized). To assess bacterial growth in the assays with RBC, the OD600 was measured after a second day inoculation with 10 μL of solution from the original plate added to 100 μL of sterile TSB followed by overnight incubation.

Hemolysis.

Peptide was serially diluted in PBS starting at a concentration of 100 μM. The final volume of peptide in each well was 50 μL. To each well, 50 μL of RBCs in PBS at $2\times10^8$ cells/mL was added. As a positive lysis control, 1% TRITON™ was used. The mixtures were incubated at 37 °C for 1 hour, after which they were centrifuged at 1000 g for 5 minutes. After centrifugation, 10 μL of supernatant was transferred to 90 μL of DI $H_2O$ in a fresh 96-well plate. The absorbance of released hemoglobin at 410 nm was recorded and the fractional hemolysis was calculated based on the 100% and 0% lysis controls.

SYTOX™ Green Cytotoxicity Assay.

WI-38 cells were grown to confluency in T-75 flasks in complete DMEM (with 15% FBS, plus antibiotics and non-essential amino acids). The day prior to cytotoxicity experiments, cells were trypsinized, removed from the flask, and pelleted. Cells were resuspended in complete DMEM and the cell count was obtained using a cell counter. The cells were then seeded at a density of 10,000 cells/well in a 96-well tissue-culture plate. Next day, in a separate 96-well plate, peptides were serially diluted in complete DMEM with 0.1% SYTOX™ Green starting at a concentration of 100 μM (1$^{st}$ well), 50 μM (2$^{nd}$ well) which was followed by serial dilution by a factor of 2:3 horizontally across the plate. To perform the cytotoxicity assay, media from wells of overnight cell culture plate was removed, washed once with PBS and treated with 50 μl of the peptide and SYTOX™ Green mixture. The plate was read for fluorescence, every 5 minutes, for an hour at the excitation wavelength of 385 nm and emission wavelength of 530 nm. MelP5, a potent MPP, that causes 100% SYTOX™ Green entry into the cells was used as a positive control to normalize the cytotoxicity of peptides tested.

Wound Infection Model.

All animal studies strictly adhered to protocol 131 which was approved by Tulane School of Medicine's Murine Institutional Animal Care and Use Committee. Female CD1 mice at 8-12 weeks of age were anesthetized via intraperitoneal injection of ketamine and xylazine at doses of 90 mg/kg and 10 mg/kg respectively. Their dorsal surface was depilated using an electric razor and scrubbed with a chlorhexidine solution. A full thickness biopsy wound was generated using a 5 mm biopsy punch (Integra). To function as a splint for the wound, a silicon (Invitrogen) ring 0.5 mm thick with an outer diameter of 10 mm and a hole with a 5 mm diameter was placed over the wound and held to the skin with a surgical adhesive. The entire silicon ring was then covered with TEGADERM™ (3M), and further adhered using 4-0 braided silk interrupted sutures (Ethicon). Mice were given 0.05 mg/kg buprenorphine immediately following surgery as well as daily for the next two days to alleviate pain from the procedure. Wound beds were infected by penetrating the TEGADERM™ with an insulin syringe and injecting 1×104 colony forming units (CFUs) of *P. aeruginosa* (PA01) and MRSA suspended in 10 μL sterile PBS directly onto the wound bed.

All bacteria used were pelleted during early exponential growth phase prior to infection. Four hours after infection mice were topically treated with 2 mM D-CONGA-Q7, or 0.025% acetic acid (vehicle control) in a 20 μL volume, by penetrating the TEGADERM™ with an insulin syringe and injecting the treatment directly on the wound bed. Treatment was administered every 8 hours for the first 5 days of infection. Mice were imaged daily for two weeks using the in vivo imaging system (IVIS)-XMRS (PerkinElmer) and bioluminescence generated from the bacteria was quantified in values of radiance (photons/sec/centimeter$^2$/steradian). Weight, activity, posture, coat condition and wound condition were monitored each day throughout the duration of the experiment to ensure the wellbeing of each mouse.

Results 13 rational variants of D-CONGA were synthesized (Table 1). D-CONGA has 13 residues and has terminal basic cassettes of RR. The nine-residue core consists of hydrophobic residues at positions 3,4, and 7 to 11 and amphipathic R at positions 5 and 6. To test if the central hydrophobic core of D-CONGA promotes its antimicrobial activity, the core was separated by inserting achiral G, beta A and polar Q at position 7 of D-CONGA to form three variants D-CONGA-G7, D-CONGA-βA7 and D-CONGA-Q7. The core hydrophobicity was also reduced by deleting A in positions 4 and 10 to form D-CONGA-ΔA4 and D-CONGA-ΔA10. To verify if the position of each hydrophobic core residue affects the activity of D-CONGA, amino acids at position 7-11 (LAFAF) and position 3-6 (WARR) were interchanged to form D-CONGA-FLIP. The importance of the basic terminal cassettes was tested by deleting the R at the C terminus, which led to the formation of D-CONGA-ΔR13. Furthermore, the effects of change in flexibility of D-CONGA on its activity was also tested by changing the residues R at position 5 and A at position 10 to L amino acids which formed D-CONGA-L (R5, A10). We have shown that antimicrobial peptides in D-form, including D-CONGA, are more effective than their L-form counterparts. To test the theory that this is due to proteolysis, L-CONGA-D (R1, R13) with all L residues except the terminal D-R in position 1 and 13 was constructed. Next, the importance of the linear structure of the peptide was tested by cyclizing L-CONGA. The linear L-CONGA was converted to cyclized form using OH at the C-terminal to form L-CONGA-OH cyclized. For another cyclized version, L-CONGA-E cyclized, a residue E was added to the C terminus to facilitate the cyclization. Lastly, to determine the necessity of amphipathic R at positions 5 and 6 for activity of D-CONGA, residues were swapped for more polar homo-arginine or less polar nor-arginine to get the last two D-CONGA variants, D-CONGA-HomoR and D-CONGA-NorR. All peptides are amidated at the C-terminus.

TABLE 3

MIC values are reported in μM peptide against gram-negative *E. coli* (EC), *P. aeruginosa* (PA), and gram-positive *S. aureus* (SA).

| Peptides | Hemolysis at 100 μM | *E. coli* | | *K. Pneumoniae* | | *S. Aureus* | | EC50, μM (WI-38) |
|---|---|---|---|---|---|---|---|---|
| | | MIC in Broth Dilution, μM RBC ($10^9$ cells/ml RBC) | | | | | | |
| | | − | + | − | + | − | + | |
| D-CONGA | 0.06 | 1 | 0.8 | 4.4 | 3.8 | 5.7 | 6.3 | 110 |
| D-CONGA-G7 | 0.07 | 1.3 | 1.4 | 1.7 | 4.4 | 6.4 | 6.9 | 235 |
| D-CONGA-Q7 | 0.07 | 1 | 1.7 | 1.1 | 1.5 | 4.2 | 3.6 | 418.4 |
| D-CONGA-βA7 | 0.02 | 1 | 1.3 | 1.4 | 1.5 | >30 | >30 | 6155 |
| D-CONGA-ΔA4 | 0.02 | 1.6 | 2.8 | 4.5 | 6.2 | 3.2 | 2.3 | 142.9 |
| D-CONGA-ΔA10 | 0.02 | 0.7 | 1.3 | 1.6 | >30 | 23.5 | 19 | 257 |
| D-CONGA-FLIP | 0.05 | 1 | 1.5 | 1.2 | 1.4 | 1.7 | 3.7 | 143.2 |
| D-CONGA-ΔR13 | 0.03 | 0.9 | 0.6 | 2.1 | 2.1 | 27.1 | >30 | 300 |
| D-CONGA-L (R5, A10) | 0.04 | 1.4 | 1.4 | 2.3 | 2.2 | >30 | >30 | 2498 |
| L-CONGA-(R1, R13) | 0.01 | 20 | 26.2 | 5.1 | 9.3 | >30 | >30 | 134.3 |
| L-CONGA-E cycl. | 0.03 | 22.9 | >30 | 20 | >30 | >30 | ND | ND |
| L-CONGA-OH cycl. | 0.7 | 5.9 | 13.3 | 2.9 | 6 | 20 | ND | ND |
| D-CONGA-HomoR | 0.06 | 1.3 | 2.2 | 8 | 5.4 | 1.7 | 2.5 | 142.5 |
| D-CONGA- NorR | 0.03 | 1.9 | 2.4 | 13.3 | 11.8 | 7.6 | 17.2 | 66.02 |

MIC values were reported in μM peptide against gram-negative *E. coli* (EC), *P. aeruginosa* (PA), and gram-positive *S. aureus* (SA). The two columns under each organism are for assays performed in the absence (−) and presence (+) of $1\times10^9$ human RBC/ml. ">30" means that sterilization was not observed at 30 μM, the highest concentration tested. The column marked "hemolysis" is the fractional hemolysis of $1\times10^8$ human RBC/ml at 100 μM peptide determined from measurements of serially diluted peptide, starting from 100 μM. The column marked "EC 50" contains the concentration of peptide that kills 50% of WI-38 human fibroblast cells assayed by entry of SYTOX™ Green DNA binding dye.

TABLE 4

Antimicrobial activity of D-CONGA and D-CONGA-Q7

| Antimicrobial Agents | Classes | Clinical Isolates | References |
|---|---|---|---|
| D-CONGA | AMP | KP (6) | *Klebsiella pneumoniae* |
| D-Q7 | AMP | KP (46) | *Klebsiella pneumoniae* |
| Ampicillin | Penicillin | KP 2146 (NDM-1) | *Klebsiella pneumoniae* |
| Gentamicin | Aminoglycoside | KP (396) | *Klebsiella pneumoniae* |
| Tobramycin | Aminoglycoside | KP (398) | *Klebsiella pneumoniae* |
| Ceftazidime | Cephalosporin | KP (St258 C2) | *Klebsiella pneumoniae* |

TABLE 4-continued

Antimicrobial activity of D-CONGA and D-CONGA-Q7

| Antimicrobial Agents | Classes | Clinical Isolates | References |
|---|---|---|---|
| Ceftriaxone | Cephalosporin | KP (ST258C3) | *Klebsiella pneumoniae* |
| Ciprofloxacin | Fluoroquinolone | KP (ST258I2) | *Klebsiella pneumoniae* |
| Meropenem | Carbapenem | KP (CRE) | *Klebsiella pneumoniae* |
| Trimethoprim | Pyrimidine Inhibitor of Dihydrofolate Reductase | (Morici) | *Klebsiella pneumoniae* |
| | | MRSA | Methicillin-resistant *Staphylococcus aureus* |
| | | AB (PDR) | *Acinetobacter baumannii* |
| | | PA (CF mucoid) | *Pseudomonas aeruginosa* |
| | | PA (CF non-mucoid) | *Pseudomonas aeruginosa* |

The antimicrobial activity of D-CONGA and D-CONGA-Q7 was compared to eight conventional antibiotics from four different classes against 14 isolates of resistant bacterial strains obtained from hospitals. These isolates included gram-negative bacterial strains of *Klebsiella Pneumoniae, Pseudomonos aeruginosa* from patients with cystic fibrosis, and pan drug-resistant *Acinetobacter baumannii* as well as gram-positive methicillin-resistant *Staphylococcus aureus*.

TABLE 5

MIC values for D-CONGA and D-CONGA-Q7 along with eight conventional antibiotics

| Isolates | Antimicrobial Agents | | | | | | | | | |
|---|---|---|---|---|---|---|---|---|---|---|
| | D-CONGA | ID-CONGA-Q7 | GEN | CAZ | AMP | CIPRO | TOB | TMP | CRO | MEM |
| | MIC, μM | | | | | | | | | |
| KP (6) | 4.2 | 3.2 | >150 | >150 | >150 | 9.4 | >150 | 13.3 | >150 | 0.2 |
| KP (46) | 4.4 | 2.2 | 1.6 | >150 | >150 | 0.2 | 3.5 | 1.3 | 1.9 | 0.4 |
| KP 2146 (NDM-1) | 14.8 | 1.8 | >150 | >150 | >150 | >150 | >150 | >150 | >150 | >150 |
| KP (ST396) | 2 | 1.9 | 2 | >150 | >150 | 0.2 | 4.6 | 124 | 1.9 | 0.3 |
| KP (St258 C2) | 64.2 | 8.9 | >150 | >150 | >150 | >150 | >150 | >150 | >150 | >150 |
| KP (ST258C3) | 91.5 | 14 | >150 | >150 | >150 | >150 | >150 | >150 | >150 | >150 |
| KP (ST258I2) | 3.2 | 1.4 | 8.3 | >150 | >150 | >150 | >150 | >150 | >150 | >150 |
| KP (CRE) | 23.4 | 2 | 5.2 | >150 | >150 | >150 | >150 | >150 | 45 | 108.3 |
| KP (Morici) | 5 | 2.4 | 1.9 | >150 | >150 | 0.2 | 7.5 | 124 | 0.3 | 0.2 |
| MRSA | 2.6 | 1.5 | >150 | >150 | >150 | 0.8 | >150 | 3.2 | >150 | >150 |
| AB (PDR) | 2.4 | 1.1 | >150 | >150 | >150 | >150 | >150 | >150 | >150 | >150 |

TABLE 5-continued

| MIC values for D-CONGA and D-CONGA-Q7 along with eight conventional antibiotics Antimicrobial Agents | | | | | | | | | | |
|---|---|---|---|---|---|---|---|---|---|---|
| Isolates | D-CONGA | ID-CONGA-Q7 | GEN | CAZ | AMP | CIPRO | TOB | TMP | CRO | MEM |
| | MIC, μM | | | | | | | | | |
| PA (mucoid) | 4.4 | 4.2 | 5.5 | 115.9 | >150 | 4.2 | 4.2 | 74.7 | 137.2 | 13.3 |
| PA (non-mucoid) | 1.3 | 1.1 | 8.3 | >150 | >150 | 5.6 | 5.9 | 74.7 | 88.45 | 4 |
| KP (398) | 31.7 | 3.8 | 1.9 | 132.7 | >150 | 0.2 | 6.9 | 17.6 | 0.2 | 0.2 |

MIC values for D-CONGA and D-CONGA-Q7 along with eight conventional antibiotics, were reported in μM peptide against 14 clinical isolates of resistant bacterial strains. ">150" means that sterilization was not observed at 150 μM, the highest concentration tested, and the strains were resistant against the antibiotics used. Sources of bacterial isolates: KP=*Klebsiella pneumoniae*. Strains 6,46, NDM-1,ST396,ST258C2,St258C3,ST258I2, 398 and CRE were isolated by Dr. J. Kolls, Tulane University from lung sputum of cystic fibrosis patients. PA=*P. aeruginosa*. Mucoid and non mucoid strains were isolated by Dr. J. Kolls, Tulane University form lung sputum of cystic fibrosis patients. *K. pneumoniae* (Morici) is ATCC #33495, provided by. Dr. L. Morici, Tulane University. MRSA is multidrug resistant *S. aureus* strain is SAP400, a USA400 strain of community acquired MRSA. AB=*A. baumanii* is a pan drug resistant (PDR) strain isolated in the Tulane Hospital in 2015.

As shown in FIG. 1, which depicts the percentage of resistant isolates sterilized by the AMPs and conventional antibiotics, AMPs D-CONGA and D-CONGA-Q were able to sterilize all the resistant isolates in the highest concentration tested.

Figure 2A:
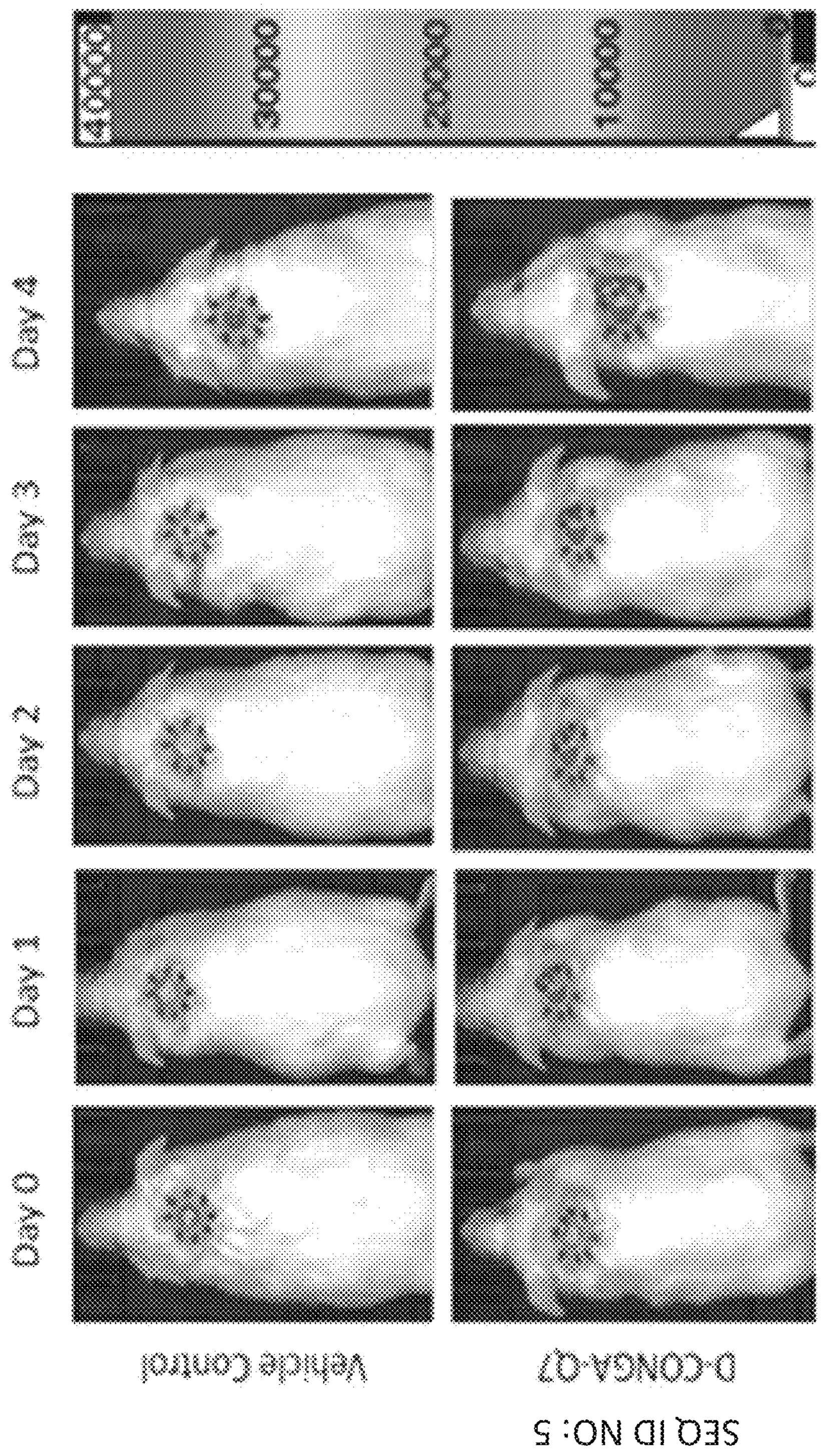
FIGS. 2A-2C show a time course of an animal model of deep surgery wound infection.
Figure 2B:
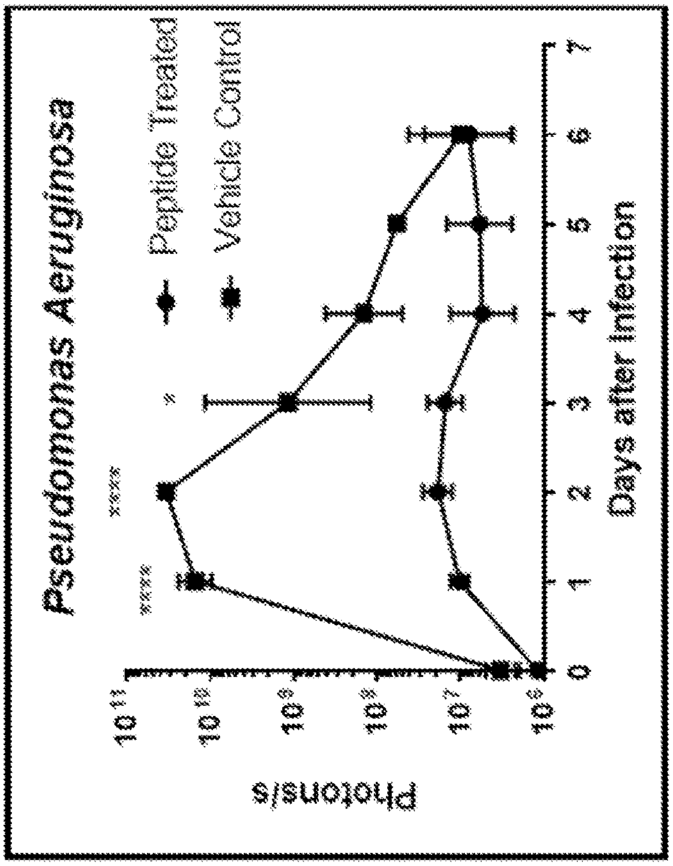
Figure 2C:
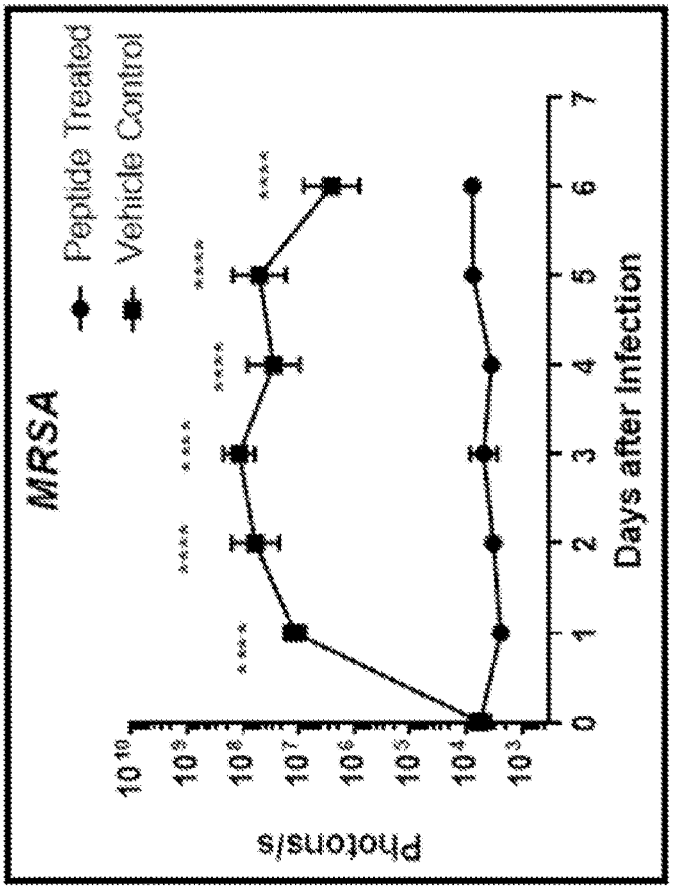

The data shown in FIGS. 2A-2C provide results from an animal model of deep surgery wound infection. Circular, dorsal puncture wounds were surgically created in healthy, adult CD1 mice, stabilized with a sutured silicon ring and covered with TEGADERM™ dressing to better mimic infection and wound healing in humans. Wounds were infected with luminescent *P. aeruginosa* and were treated with D-CONGA-Q7 peptide or vehicle control every 8 hours until Day 4. An IVIS whole animal imager was used to measure luminescence in all animals once per day for 13 days after infection. FIGS. 2A-2C indicate that the peptide treatment was able to reduce infection as compared to vehicle control.

Figure 3:
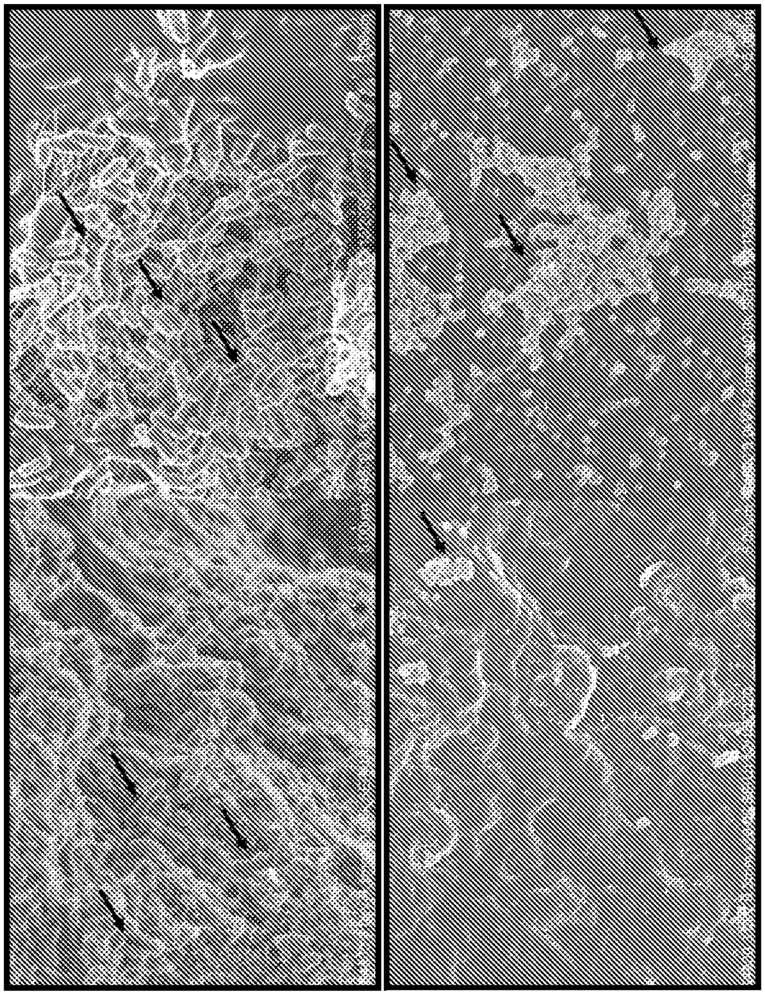
FIG. 3 is a set of representative scanning electron microscopy images of glutaraldehyde-fixed TEGADERM™ dressings that were removed from experimental animals on Day 3. Scale bars are 5 μm in all images. The top two images show TEGADERM™ removed from the vehicle-treated control animals infected with *P. aeruginosa*. Data for these animals is shown in FIGS. 2A and 2B. Black arrows in these images show dense clusters of rod-like objects that are indistinguishable in size and shape from *P. aeruginosa* bacteria and *P. aeruginosa* biofilms. The bottom two images show TEGADERM™ removed from the peptide-treated (D-CONGA-Q7; SEQ ID NO: 5) control animals infected with *P. aeruginosa*. Data for these animals is shown in FIGS. 2A and 2B. No objects consistent with *P. aeruginosa* bacteria are observed. Black arrows in these images indicate non-bacterial debris.

We also examined the TEGADERM™ dressing removed from the adult CD1 mice tested in the deep surgery would infection model discussed above. The TEGADERM™ dressing was fixed with glutaraldehyde-fixed and scanned. The images show that D-CONGA-Q7 inhibited biofilm formation and significantly eliminated the infecting *P. aeruginosa* (see FIG. 3). The black arrows on the top two images of FIG. 3 show vehicle controls with abundant biofilms and rod-like *P. aeruginosa* in all samples. The black arrows in the bottom two images of FIG. 3 point out TEGADERM™ from a wound treated 3 times a day with D-CONGA-Q7 peptides. The images show few individual bacteria. Importantly, no biofilm is observed, and only the TEGADERM™ adhesive is visible.

Figure 4A:
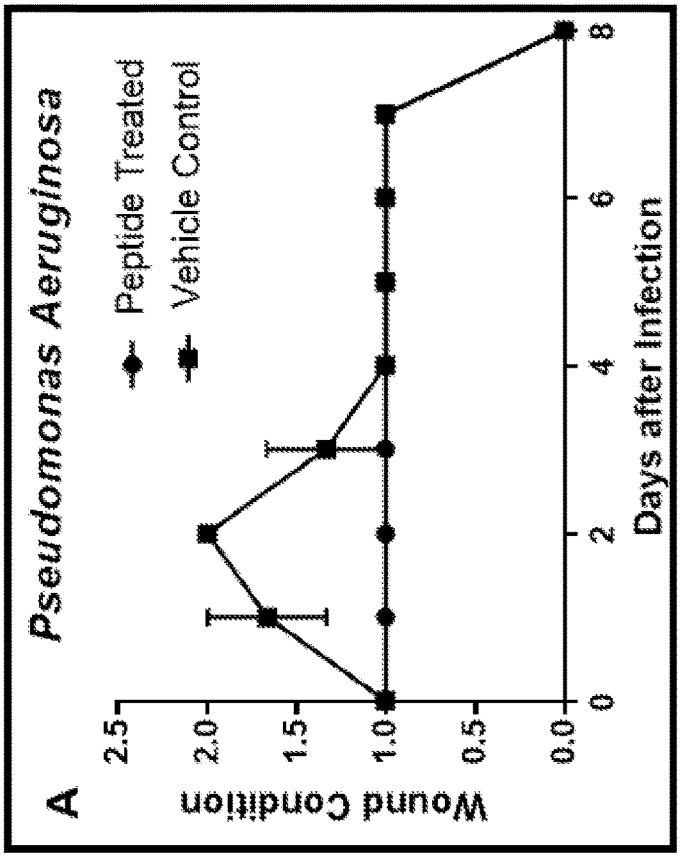
FIGS. 4A and 4B are graphs showing the wound condition of each mouse peptide treated (D-CONGA-Q7; SEQ ID NO: 5) or vehicle control treated that was monitored everyday throughout infection with either *P. aeruginosa* (FIG. 4A) or MRSA (FIG. 4B). Wound condition was evaluated using a number system from 0-4. 0=the absence of inflammation or discharge, 1=light inflammation and slight discharge, 2=obvious inflammation, discharge, and discoloration, 3=intermediate inflammation, 4=heavy inflammation, discoloration, and the presence of pus.
Figure 4B:
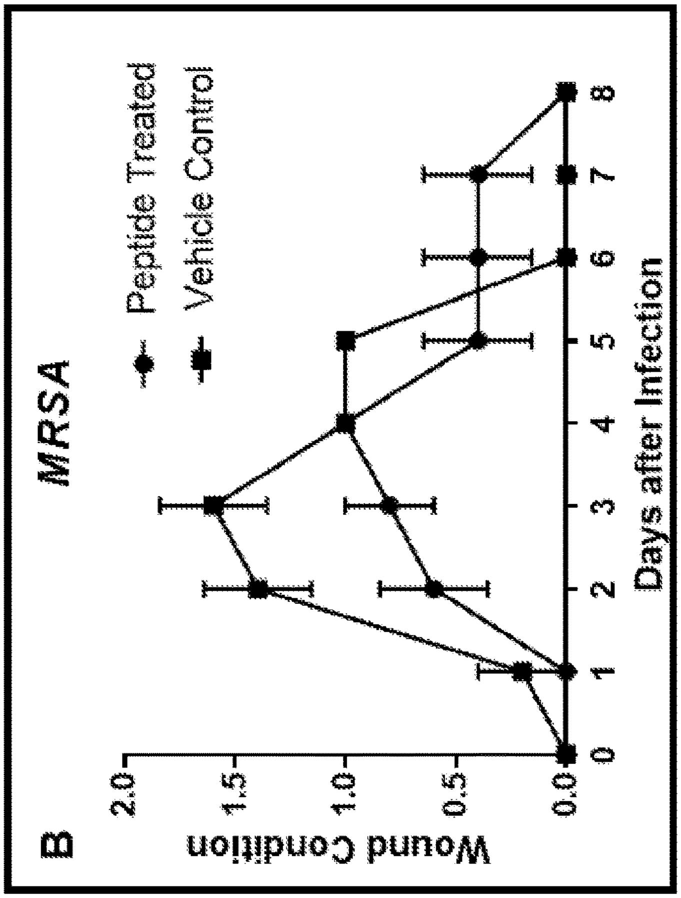

We also monitored the wound condition of each mouse everyday throughout the deep surgery wound infection experiment. The wound condition was graded on a scale from 0 (indicating no inflammation or discharge) to 4 (indicating significant inflammation and discharge). As is shown in FIGS. 4A and 4B, the wound condition of mice treated with D-CONGA-Q7 was reduced to 0 within 8 days after infection with either *P. aeruginosa* (FIG. 4A) or MRSA (FIG. 4B), indicating no inflammation or discharge.

CONCLUSION

We have demonstrated that variations in the sequence and structure of D-CONGA can affects its antimicrobial activity. Several of the changes we made to D-CONGA retain the activity of the original D-CONGA peptide, whereas other changes resulted in a peptide with significantly improved bactericidal activity and reduced cytotoxicity. Out of the 13 variants we synthesized and characterized, 11 were evaluated for their cytotoxic effects. 10 out of the 11 variants showed lower toxicity against WI-38 cells. 11 out of the 13 variants had minimum hemolysis of less than 1%. The experiments performed in the presence and absence of RBC demonstrated that most variants had excellent activity against gram-negative bacteria, *K. Pneumonia*, and *E. coli*. Still, only 5 out of 13 variants could sterilize gram-positive *S. aureus* with concentrations less than 10 uM. The best peptides among the 13 variants based on minimum hemolysis and low toxicity were D-CONGA-G7, D-CONGA-Q7, and D-CONGA-βA7. Hence, the splitting of the hydrophobic core of the D-CONGA resulted in decreased cytotoxicity. Although D-CONGA-βA7 was the least toxic of the variants, it completely lost its activity against gram-positive *S. aureus*. The other two had similar antibacterial activity but D-CONGA-Q7 had lesser toxicity which alludes to the significance of sequence composition in the function of AMP. D-CONGA-Q7 also had better activity against all the bacterial strains tested and lower cytotoxicity against human fibroblast, WI-38 cells, than even D-CONGA. In fact, EC50 against WI-38 cells for D-CONGA-Q7 is four times higher than that of D-CONGA. Thus, D-CONGA-Q7, which varies from the lead peptide, D-CONGA, with only one amino acid at position 7, exhibited broad-spectrum activity, low cytotoxicity and minimum hemolysis.

D-CONGA-Q7 represents a new, potent, broad-spectrum treatment against resistant bacteria often encountered in hospital settings. We confirmed the superior antimicrobial activity of D-CONGA-Q7 in a head-to-head evaluation with D-CONGA and eight conventional antibiotics against 14 clinical isolates of resistant bacterial strains. The eight antibiotics belonged to five different classes of Penicillin (Ampicillin), Aminoglycoside (Gentamycin and Tobramycin), Cephalosporin (Ceftazidime and Ceftriaxone), Carbapenem (Meropenem), and Pyrimidine inhibitor (Trimethoprim). The 14 resistant bacterial strains were obtained from clinical isolates, mainly from patients in Tulane Hospital, New Orleans. The clinical isolates consisted of 10 *K. pneumonia* strains, a MRSA strain, a PDR *A. baumannii* strain and one strain each of mucous and nonmucous *P. aeruginosa* from patients of cystic fibrosis.

D-CONGA-Q7 outperformed D-CONGA as well as major conventional antibiotics in vitro. D-CONGA-Q7 sterilized even the two *K. Pneumonia* strains resistant to all the antibiotics and had high MIC with D-CONGA at a concentration less than 15 uM. The excellent bactericidal activity of D-CONGA-Q7 outperforms the lead peptide, D-CONGA. D-CONGA-Q7 is expected to exhibit similar superior activity against biofilms and to inhibit bacterial infection in animal wound model in vivo. Taken collectively, the results demonstrate the ability of D-CONGA-Q7 to sterilize several different resistant bacterial strains. Consequently, D-CONGA-Q7 can be administered to treat bacterial strains exhibiting antibiotic resistance to other known antibacterial therapies.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. All publications, patents, and patent applications mentioned in the above specification are hereby incorporated by reference to the same extent as if each individual publication, patent or patent application was specifically and individually indicated to be incorporated by reference in its entirety.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Other embodiments are within the claims.

The invention claimed is:

1. A polypeptide having at least 95% sequence identity to the sequence of any one of SEQ ID NOs: 3-7 and 17-21.

2. The polypeptide of claim 1, wherein:
a) the polypeptide is an antimicrobial peptide;
b) the polypeptide disrupts the cellular membrane of a microbial pathogen;
c) the polypeptide comprises one or more D-amino acids, one or more L-amino acids, or a mixture of D- and L-amino acids, wherein optionally the one or more D-amino acids are independently selected from the group consisting of D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL;
d) the polypeptide comprises one or more derivatized amino acids, wherein optionally the one or more derivatized amino acids are selected from the group consisting of N-imbenzylhistidine, 4-hydroxyproline, 5-hydroxylysine, 3-methylhistidine, homoserine, and ornithine;
e) the polypeptide is 10 to 20 amino acids long; and/or
f) the polypeptide is a cyclized polypeptide.

3. A composition comprising the polypeptide of claim 1, a polynucleotide encoding the polypeptide, or a vector comprising the polynucleotide.

4. The composition of claim 3, wherein:
a) the composition further comprises a pharmaceutically acceptable carrier, excipient, or diluent and/or a therapeutic compound, wherein optionally the therapeutic compound is an antimicrobial agent or an antifungal agent;
b) the composition is a liquid or a solid; and/or
c) the polypeptide is incorporated in the composition or coated thereon, wherein optionally said composition is a medical device, a cuff, a dressing material, a mesh, a hernia patch, a wound dressing, a bandage, a syringe, gloves, or a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface.

5. A kit comprising the polypeptide of claim 1 and, optionally, an antimicrobial agent.

6. The kit of claim 5, wherein said antimicrobial agent is an antibacterial agent or an antifungal agent.

7. The kit of claim 6, wherein said antibacterial agent is a polymyxin.

8. The polypeptide of claim 1, wherein the polypeptide has 97% sequence identity to any one of SEQ ID NOs: 3-7 and 17-21.

9. The polypeptide claim 1, wherein the polypeptide has the sequence of SEQ ID NO: 5.

10. A polypeptide having at least 90% sequence identity to the sequence of any one of SEQ ID NOs: 12, 13, 15, 16, and 26-29.

11. A composition comprising the polypeptide of claim 10, a polynucleotide encoding the polypeptide, or a vector comprising the polynucleotide.

12. A polypeptide having at least 85% sequence identity to the sequence of any one of SEQ ID NOs: 8 and 22.

13. A composition comprising the polypeptide of claim 12, a polynucleotide encoding the polypeptide, or a vector comprising the polynucleotide.

14. The composition of claim 3, wherein the composition is formulated for intravenous administration.

15. The composition of claim 11, wherein the composition is formulated for intravenous administration.

16. The composition of claim 13, wherein the composition is formulated for intravenous administration.

17. A method of treating a microbial infection comprising administering the composition of claim 3 to a subject in need thereof or contacting the composition to the subject.

18. The method of claim 17, wherein:
a) said microbial infection is a fungal or bacterial infection;
b) the subject is a human or a non-human mammal;
c) the composition treats a wound in the subject; and/or
d) the composition is administered or contacted topically.

19. A method of manufacturing the polypeptide of claim 1, comprising:
a) chemically synthesizing the polypeptide; or
b) expressing the polypeptide in a cell that has been transformed with a polynucleotide encoding the polypeptide and recovering the polypeptide from the cell or a culture media surrounding the cell.

* * * * *